(12) United States Patent
Clement et al.

(10) Patent No.: US 8,815,844 B2
(45) Date of Patent: Aug. 26, 2014

(54) MITOCHONDRIAL ACTIVITY INHIBITORS OF CANCER-INITIATING CELLS AND USE THEREOF

(75) Inventors: Virginie Clement, Ferney-Voltaire (FR); Ivan Radovanovic, Geneva (CH)

(73) Assignees: Universite de Geneve, Geneva (CH); Hopitaux Universitaires de Geneve, Geneva (CH)

( * ) Notice: Subject to any disclaimer, the term of this patent is extended or adjusted under 35 U.S.C. 154(b) by 56 days.

(21) Appl. No.: 13/321,379

(22) PCT Filed: May 20, 2010

(86) PCT No.: PCT/IB2010/052237
§ 371 (c)(1),
(2), (4) Date: Nov. 18, 2011

(87) PCT Pub. No.: WO2010/134039
PCT Pub. Date: Nov. 25, 2010

(65) Prior Publication Data
US 2012/0071465 A1   Mar. 22, 2012

(30) Foreign Application Priority Data
May 20, 2009  (EP) .................................. 09160719

(51) Int. Cl.
*A61K 31/55* (2006.01)
*C07D 321/00* (2006.01)

(52) U.S. Cl.
USPC ........... 514/217; 514/453; 514/450; 514/365; 549/283; 549/367

(58) Field of Classification Search
CPC .................. A61K 31/343; A61K 51/0419
USPC .......... 514/217, 450, 453, 365, 532; 548/204, 548/401
See application file for complete search history.

(56) References Cited

FOREIGN PATENT DOCUMENTS

| WO | 2002/043652 A2 | 6/2002 |
| WO | 2002/058684 A2 | 8/2002 |
| WO | 2006/024491 A1 | 3/2006 |
| WO | 2007/139961 A1 | 12/2007 |
| WO | 2008/031171 A1 | 3/2008 |
| WO | 2009/066258 A1 | 5/2009 |
| WO | 2009/148623 A2 | 12/2009 |

OTHER PUBLICATIONS

Chang et al. Invest Ophthalmol Vis Sci. 2007;48:2895-2902).*
Friedman et al. Clin Cancer Res 2000;6:2585-2597.*
http_www.neurosurgicalatlas Jul. 30, 2013.*
Beaney et al. (J. Clinical Oncology (2005); 23(16S) (Jun. 1 Supplement), 2005: 1535).*
Pilkington et al. Seminars in Cancer Biology 18; (2008) 226-235).*
www.medicalook.com 2013.*
Rivera et a. Frontiers in Oncology, Mini Review Article Apr. 8, 2013.*
Bilir Ayhan et al: "Potentiation of cytotoxiCity by combination of imatinib and chlorimipramine in glioma", International Journal of Oncology, vol. 32, No. 4, Apr. 1, 2008, pp. 829-839.
Clement Virginie et al: "Marker-independent identification of glioma-initiating cells", Nature Methods, vol. 7, No. 3, Mar. 1, 2010, pp. 224-228.
Costas G Hadjipanayis et al: "Tumor initiating cells in malignant gliomas: biology and implications for therapy", Journal of Molecular Medicine, vol. 87, No. 4, Feb. 3, 2009, pp. 363-374.
Daley E et al: "Chlorimipramine: A novel anticancer agent with a mitochondrial target", Biochemical and Biophysical Research Communications, vol. 328, No. 2, Mar. 11, 2005, pp. 623-632.
Gyulkhandanyan Armen et al: "Shift in the localization of sites of hydrogen peroxide production in brain mitochondria by mitochondrial stress", Journal of Neurochemistry, vol. 90, No. 2, Jul. 1, 2004, pp. 405-421.
Ling Gao et al: "Mitochondrial Pathophysiology, Reactive Oxygen Species, and Cardiovascular Diseases", Vet Clin North Am Small Anim Pract, vol. 38, No. 1, Jan. 1, 2008, pp. 137-155.
Ludwig Lynda M et al: "Preconditioning by isoflurane is mediated by reactive oxygen species generated from mitochondrial electron transport chain complex III", Anesthesia and Analgesia, vol. 99, No. 5, Nov. 1, 2004, pp. 1308-1315.
Parker Katharine A et al: "Apoptosis of human malignant glioma-derived cell cultures treated with clomipramine hydrochloride, as detected by annexin-V assay", Radiology and Oncology, vol. 40, No. 2, Jan. 1, 2006, pp. 87-93.
Pilkington G J et al: "Approaches to mitochondrially mediated cancer therapy", Seminars in Cancer Biology, vol. 18, No. 3, Jun. 1, 2008, pp. 226-235.
Pilkington Geoffrey J et al: "The role of tricyclic drugs in selective triggering of mitochondrially-mediated apoptosis in neoplastic glia: a therapeutic option in malignant glioma?", Radiology and Oncology, vol. 40, No. 2, Jan. 1, 2006, pp. 73-85.
Ueki M et al: "Antifungal Inhibitors of Mitochondrial Respitation: Discovery and Prospects for Development", Current Opinion in Antiinfective Investigational Drugs, vol. 2, No. 4, Jan. 1, 2000 , pp. 387-398.

* cited by examiner

*Primary Examiner* — Shirley V Gembeh
(74) *Attorney, Agent, or Firm* — Quarles & Brady, LLP

(57) ABSTRACT

The present invention relates to the compounds useful in the prevention and/or treatment of tumors. More specifically the present invention relates to inhibitors of the activity of the electron transport chains and/or the mitochondrial TCA cycle in glioma-initiating cells (GICs) for use in a method for preventing and/or treating tumors presenting glioma-initiating cells (GICs) in a subject who has undergone a prior removal of a tumor glioma bulk. The present invention further provides a pharmaceutical composition containing the inhibitors of the invention and a screening method for identifying the inhibitors of the invention.

3 Claims, 13 Drawing Sheets

Primary GBM-3          Primary GBM-16

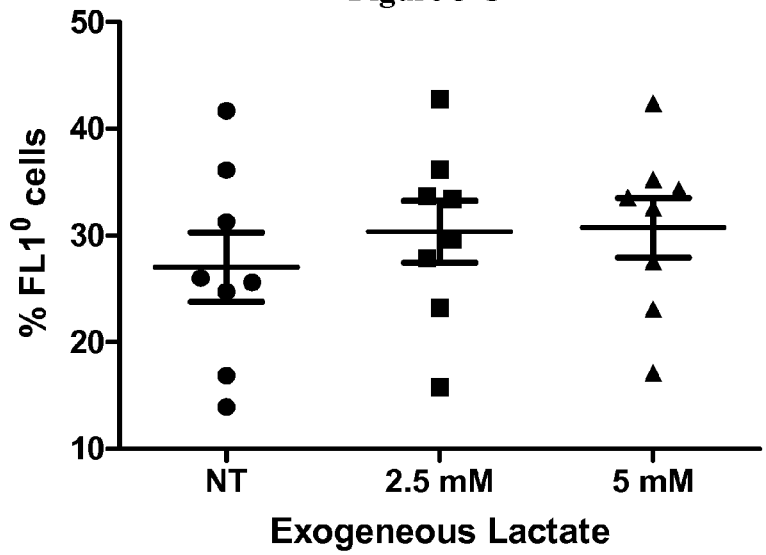
Figure 3 C
Figure 3 D
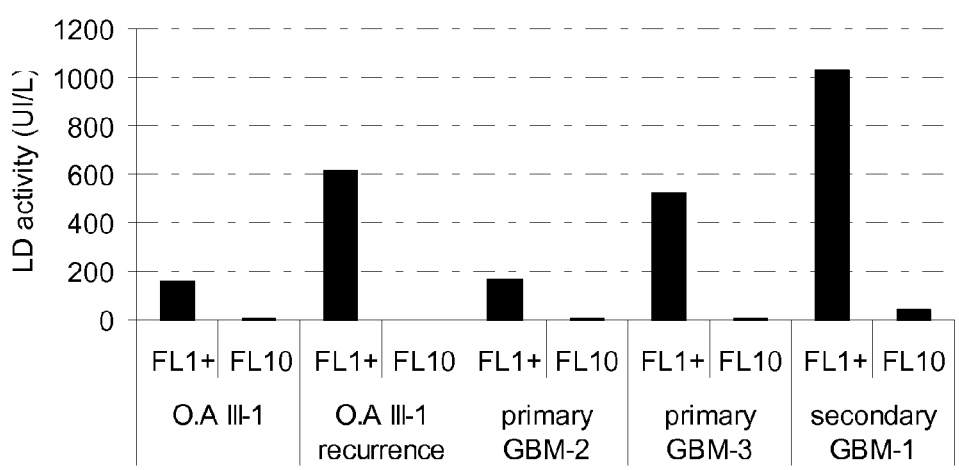

Figure 6 A1
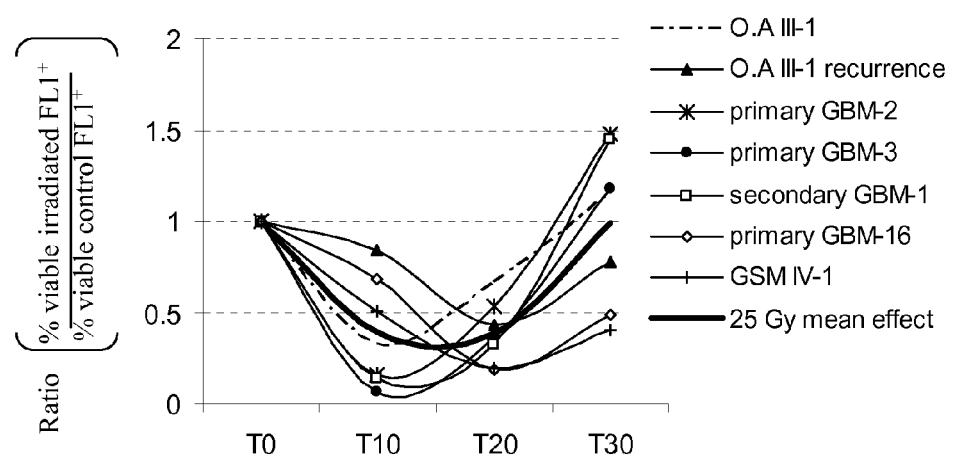
Figure 6 A2
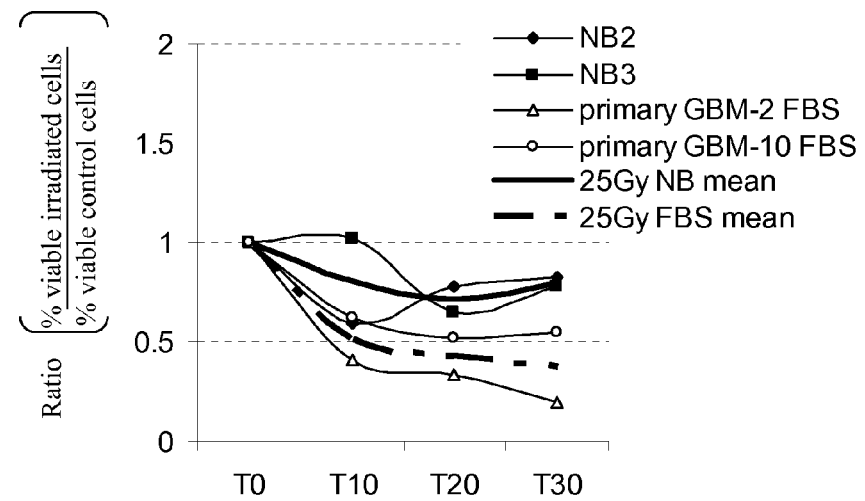

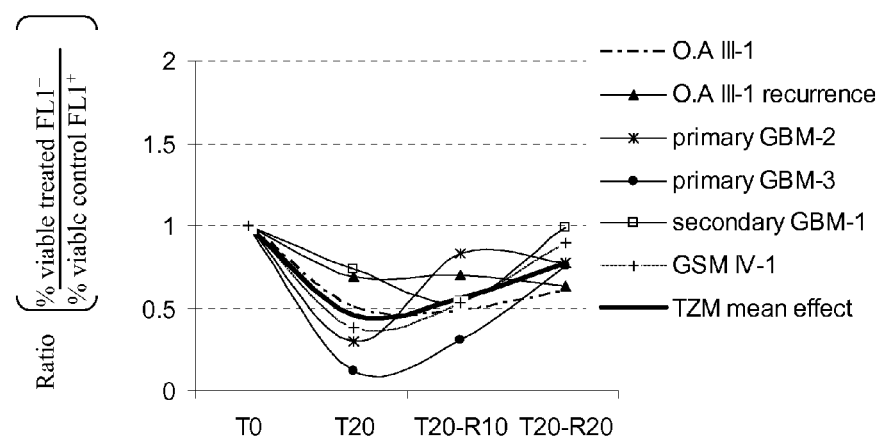
Figure 6 B1

Figure 6 C1
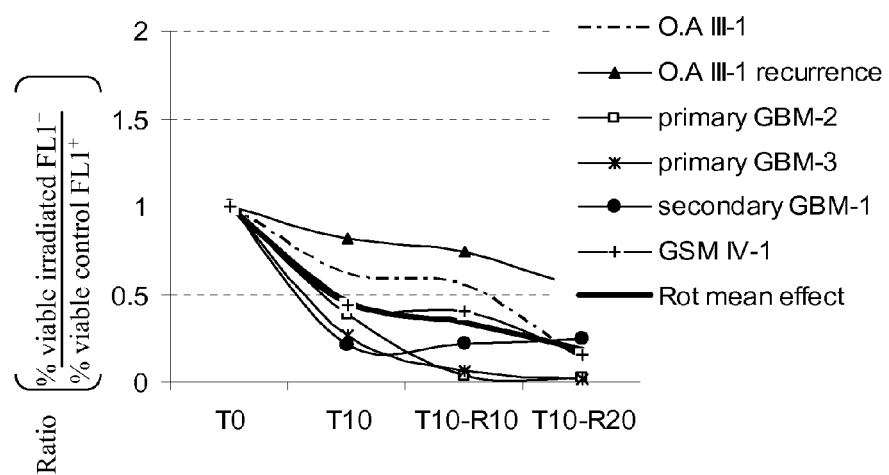
Figure 6 C2
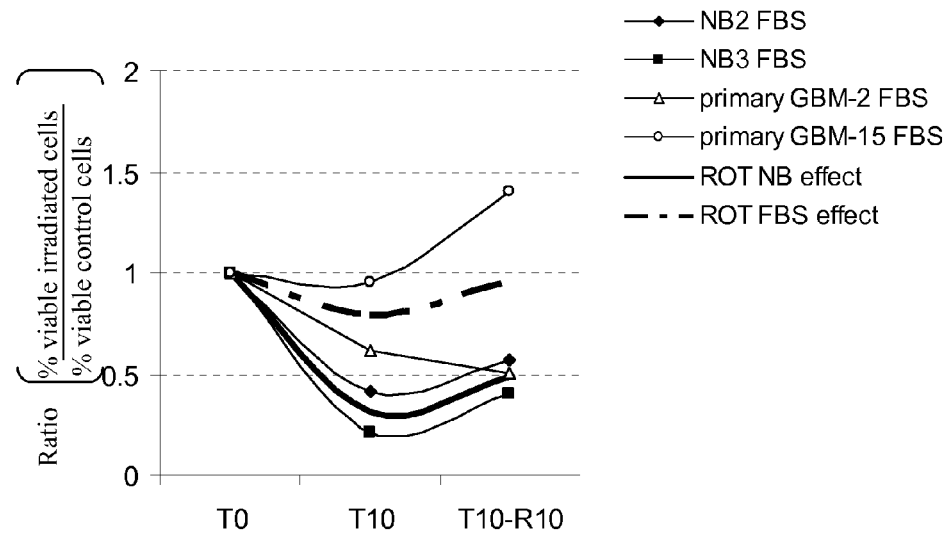

Figure 6 D1
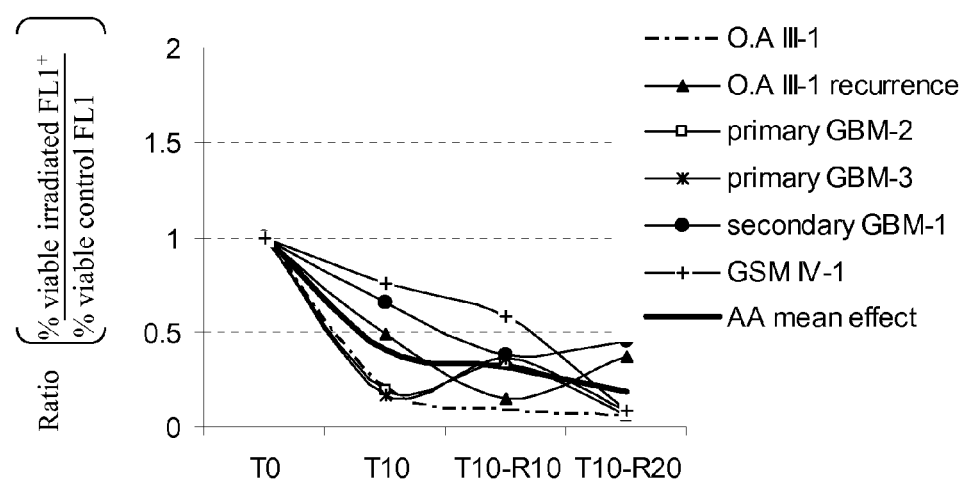
Figure 6 D2
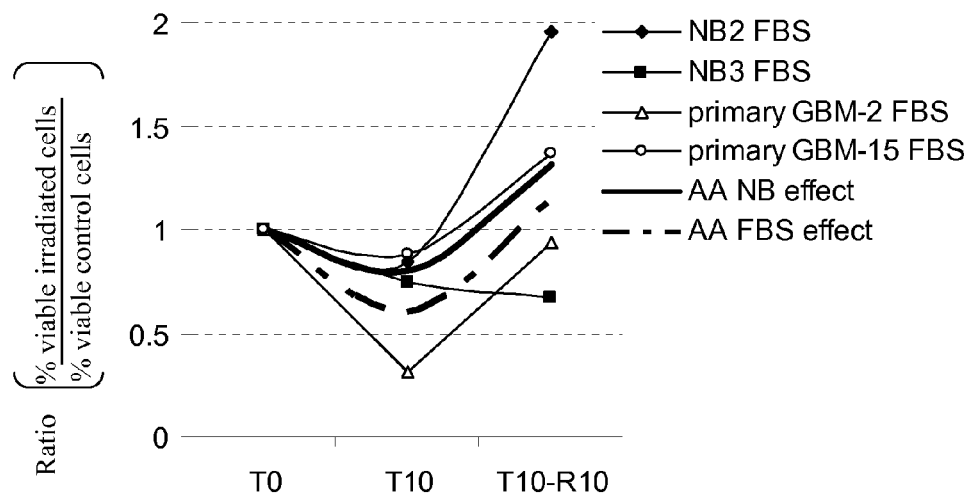

Figure 6 E1
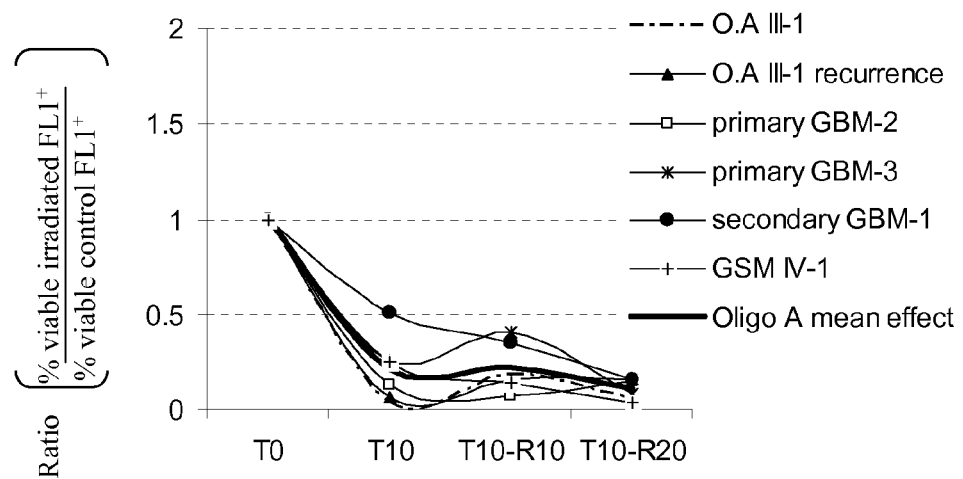
Figure 6 E2
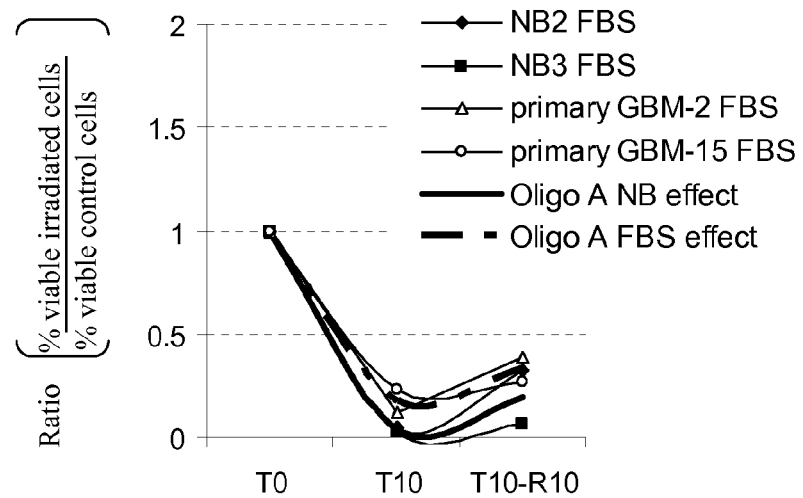

Figure 6 F1
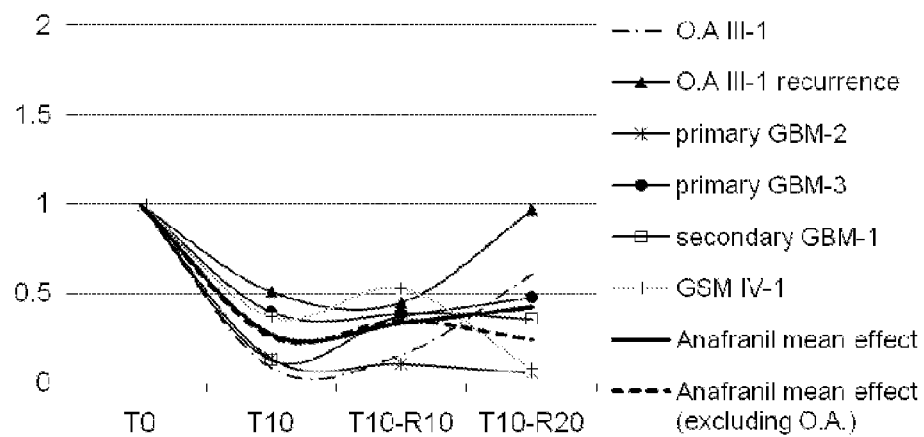
Figure 6 F2
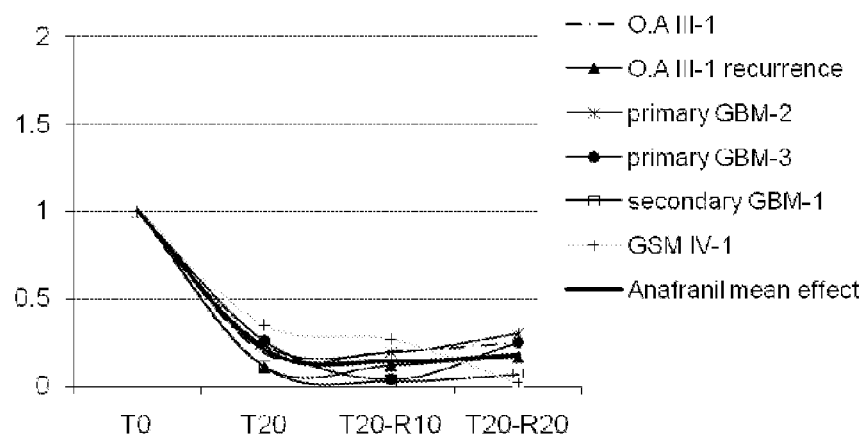

MITOCHONDRIAL ACTIVITY INHIBITORS OF CANCER-INITIATING CELLS AND USE THEREOF

CROSS REFERENCE TO RELATED APPLICATIONS

This application represents the national stage application of International Application PCT/IB2010/052237 filed May 20, 2010, which claims the benefit of European Patent Application No. 09160719.2, filed May 20, 2009, all of which are incorporated herein by reference in their entirety for all purposes.

FIELD OF THE INVENTION

The present invention relates to the compounds useful in the prevention and/or treatment of tumours. More specifically the present invention relates to inhibitors of the activity of the electron transport chains and/or the mitochondrial TCA cycle in glioma-initiating cells (GICs) for use in a method for preventing and/or treating tumours presenting glioma-initiating cells (GICs) in a subject who has undergone a prior removal of a tumour glioma bulk. The present invention further provides a pharmaceutical composition containing the inhibitors of the invention and a screening method for identifying the inhibitors of the invention.

BACKGROUND OF THE INVENTION

Glioma remains the most frequent brain tumours in adults. The malignant form of glioma, grade IV also referred to as glioblastoma multiforme (GBM) is notoriously hard to treat. It returns in most cases despite virtually all current therapies, which include surgery, radiation and chemotherapy. Survival rates are very low, for example 14.6 months on average even when combining chemotherapy with radiation. No environmental risk factors have been identified and little is known about the biological mechanisms involved in the initiation and progression phases of these brain tumours.

In 1930, Otto Warburg proposed that cancer originates when a nonneoplastic cell adopts an anaerobic metabolism after two successive phases: (1) an irreversible injury of respiration and (2) the successful replacement of the irretrievably lost of respiration by glycolysis. According to this theory, the majority of cancer cells are believed to preferentially produce energy by producing lactacte from glucose under aerobic conditions, phenomenon commonly named "aerobic glycolysis" and referred as the Warburg's effect. Therefore, developing cancer treatment targeting this aerobic glycolysis metabolism pathway, which would allow the remodeling of the metabolism process towards an active respiration and production of energy by the mitochondria has raised interest in the last decade.

Some publications suggest the mitochondria of glioma cells to be a potential target for cancer chemotherapy (Daley et al., 2005, *Biochemical and Biophysical Research Communications,* 328 (2):623-632; Pilkington et al., 2008, *Seminars in cancer biology England,* 18 (3):226-235). These publications disclose a treatment, which involves clomipramine or in general tricyclics agents as inhibitors of the mitochondrial complex III and potential chemotherapy for glioma cells (cancer cells), without further radiotherapy or surgery. Said inhibitors induce apoptosis mediated by the activation of the mitochondrial route i.e. via the release of cytochrome C and activation of caspase-3. This kind of therapy would be possible because glioma cells (cancer cells) have a different metabolism than the normal cells.

WO 2008/031171 (Griffith University) also discloses some anti-cancer compounds and methods for treating or preventing cancer. In particular, pro-oxidant anti-cancer compounds are disclosed, such as pro-oxidant forms of vitamin E, which selectively interact with complex II (succinate-ubiquinone oxidoreductase) of the mitochondrial respiratory chain of cancerous cells, generate reactive oxygen species and induce apoptosis of those cells.

However, this therapeutic strategy makes the assumption that the biology and metabolism of every single cancer cell (such as glioma cells) is similar and unfortunately did not provide a significant progress in the treatment of glioma.

Although the exact cellular origin of gliomas remains unclear it is proposed that only a fraction of cancer cells with stem cell properties, usually named cancer stem cells (CSC), has true tumorigenic potential and constitutes a discrete reservoir of cancer initiating cells in glioma. The recent identification of Stem-like Cells (SC) in a number of human cancers like acute myeloid leukemias (AML), breast, ovarian and brain tumours has renewed interest in the hypothesis that cancers may arise from somatic mutations in adult stem/progenitor cells.

Brain tumour cancer initiating cells, know as Glioma-initiating cells (GICs) were initially identified as $CD133^+$ cells but recent studies demonstrate a relative lack of specificity of this marker. These cells are heterogeneous populations of cells with different tumorigenic capacity, some tumour cells having a superior tumour initiating and propagating ability. Glioma-initiating cells (GICs) are responsible for the initiation and recurrence of gliomas. The role of glioma-initiating cells with stem cell properties has not yet been well investigated. These cells display characteristic stem cell features including self renewal capacity at single cell level, multipotency with evidence of astroglial, neuronal and oligodendroglial differentiation in vitro and tumorigenicity in vivo. As other human cancers, gliomas contain cellular hierarchies on the top of which tumour initiating and propagating cells with stem cell properties (called cancer stem cells-CSC) seem to control tumour growth. This minor population of cancer stem-like cells, GICs account only for about 5% of tumour cells (gliomas), may represent the source of tumour cell expansion, recurrence and metastasis, thus determining the biological behaviour of tumours including proliferation, progression, and subsequently response to therapy.

Targeting glioma-initiating cells remains challenging due to their rarity, instability in culture and the absence of robust tracer agents. So far, no efficient treatment against glioma-initiating cells has shown a complete eradication of the glioma growth or absence of recurrence in any of the orthotopic xenograft and/or transgenic mouse model. The resistance of glioma-derived tumour-initiating cells to conventional radiotherapy has been demonstrated (Bao et al., 2006; Clement et al., 2007). For example it is known that glioma-initiating cells are resistant to chemotherapeutic agents like temozolomide. These data might explain the inevitable recurrence of gliomas and define glioma-initiating cells as novel targets to overcome the resistance to conventional therapy in this disease.

For the moment no efficient treatment against recurrence of glioma is currently available. There is still a need to find an efficient treatment specifically directed to glioma-initiating cells. However, before identifying any efficient molecule against glioma-initiating cells and obtaining any significant improvement in glioma therapy, it is essential to better and deeper understand the cellular and molecular mechanisms of glioma-initiating cells.

SUMMARY OF THE INVENTION

Surprisingly the Applicants have demonstrated that the glioma-initiating cells have different metabolism from other cancer cells, such as glioma.

Thus the present invention provides an inhibitor of the activity of the electron transport chains and/or the mitochondrial TCA cycle in glioma-initiating cells (GICs) for use in a method for preventing and/or treating tumours presenting glioma-initiating cells (GICs) in a subject who has undergone a prior removal of a tumour glioma bulk, wherein said inhibitor fulfils the following criteria:
1) a viability of GICs decreases for more than 50% during the exposure to said inhibitor of the activity of the electron transport chains and/or the mitochondrial TCA cycle during a maximum of 20 days,
2) a recovery of GICs is less than 0.2 fold during the recovery phase of a maximum of 20 days, and
3) the viability of normal brain cells is sustainable and recoverable during and after the exposure to the said inhibitor of the activity of the electron transport chains and/or the mitochondrial TCA cycle.
and whereby, said inhibitor of the activity of the electron transport chains and/or the mitochondrial TCA cycle blocks the production of energy by GICs.

Further, the present invention provides a pharmaceutical composition for preventing and/or treating tumours presenting glioma-initiating cells (GICs) in a subject who has undergone a prior removal of a tumour glioma bulk, comprising at least one inhibitor of the activity of the electron transport chains and/or the mitochondrial TCA cycle according to the invention, and one or more pharmaceutically acceptable diluents or carriers.

Another object of the present invention is a method of preventing and/or treating tumours presenting glioma initiating cells in a subject who has undergone a prior removal of a tumour glioma bulk, said method comprises the administration of a therapeutically effective amount of an inhibitor of the activity of the electron transport chains and/or the mitochondrial TCA cycle, wherein said inhibitor fulfils the following criteria:
1) a viability of GICs decreases for more than 50% during the exposure to said inhibitor of the activity of the electron transport chains and/or the mitochondrial TCA cycle during a maximum of 20 days,
2) a recovery of GICs is less than 0.2 fold during the recovery phase of a maximum of 20 days, and
3) the viability of normal brain cells is sustainable and recoverable during and after the exposure to the said inhibitor of the activity of the electron transport chains and/or the mitochondrial TCA cycle,
and whereby, said inhibitor of the activity of the electron transport chains and/or the mitochondrial TCA cycle blocks the production of energy by GICs.

Additionally the invention provides a screening method for identifying inhibitors of the activity of the electron transport chains and/or the mitochondrial TCA cycle in glioma-initiating cells (GICs), said method comprises contacting the $FL1^+$ cells, isolated from a tumour cell sample, and normal brain cells with an inhibitor to be screened, wherein said inhibitor fulfils the following criteria:

1) a viability of $FL1^+$ cells decreases for more than 50% during the exposure to said inhibitor during a maximum of 20 days,
2) a recovery of $FL1^+$ cells is less than 0.2 fold during the recovery phase of a maximum of 20 days, and
3) the viability of normal brain cells is sustainable and recoverable during and after the exposure to the said inhibitor.

The invention also encompasses a kit for screening inhibitors of the activity of the electron transport chains and/or the mitochondrial TCA cycle in glioma-initiating cells (GICs) fulfilling the following criteria:
1) a viability of $FL1^+$ cells decreases for more than 50% during the exposure to said inhibitors during a maximum of 20 days,
2) a recovery of $FL1^+$ cells is less than 0.2 fold during the recovery phase of a maximum of 20 days, and
3) the viability of normal brain cells is sustainable and recoverable during and after the exposure to the said inhibitors,
and useful in the treatment of tumours presenting glioma initiating cells, wherein said kit comprises primary CIC cultures, primary adherent glioma cells, normal cells and at least one standard inhibitor of the activity of the Complex (I) or Complex (III) of the mitochondrial electron transport chain selected from the group comprising rotenone and antimycin A.

BRIEF DESCRIPTION OF THE FIGURES

FIG. 6 shows the effects of drugs in an in vitro recurrence assay as described in Example 2 and expressed as a ratio of percentages viable treated $FL1^+$ to viable control $FL1^+$ (1) or a ratio of percentages viable treated cells to viable control cells (2). A: γ-radiation 25 Gy. B: Temozolomide 25 μM (TMZ). C: Rotenone 5 μM (Rot); D: Antimycin A 5 μM (AA). E: Oligomycin A/B 5 μM (Oligo A). F: Clomipramine also named anfranil (10 μM). Tx refers to the treatment for a x period of time: for example 10 days (T10), 20 days (T20) and R refers to the recovery phase for a certain period of time like 10 days (R10) and 20 days (R20).

DETAILED DESCRIPTION OF THE INVENTION

Figure 1:
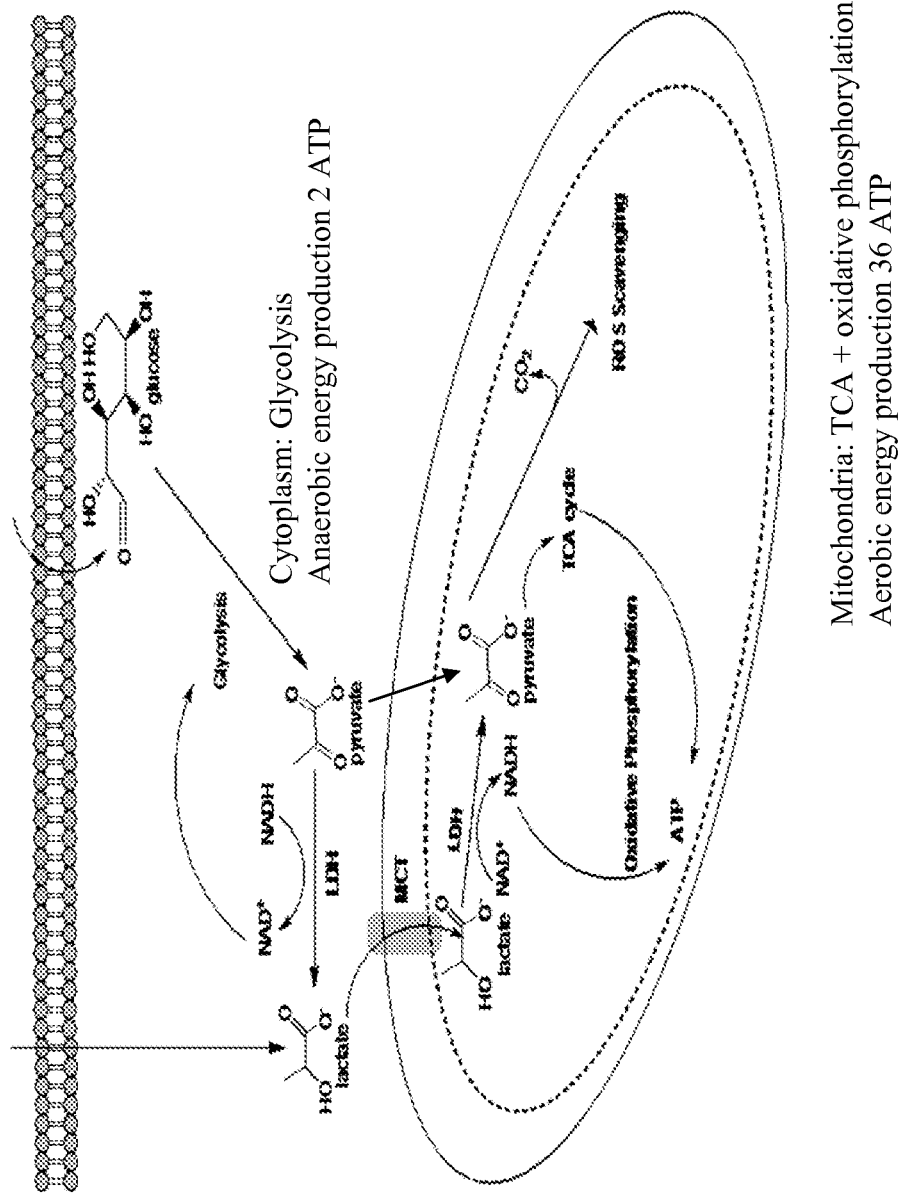
FIG. 1 represents a scheme of the anaerobic and aerobic pathways in mammalian cells (modified from Lemire et al., 2008, PLoS ONE, vol. 3 (2), e1250).

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular form "a", "an" and "the" include plural references unless the context clearly dictates otherwise.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder, such as cancer, preferably glioma. However, in other embodiments, the subject can be a normal subject or a subject who has already undergone a treatment, such as for example a prior removal of a tumour glioma bulk. The term does not denote a particular age or sex. Thus, adult and newborn subjects, whether male or female, are intended to be covered.

The identification of agents, such as inhibitors, useful in the treatment of cancers presenting glioma initiating cells implies the use of a reliable selection method to identify, isolate and characterize the whole cancer-initiating cells (CICs) reservoir. Methods which use preferentially cancer cell lines, such as glioma cell lines, predetermined by arbitrary markers (like CD133 as a read-out of stemness) that are generally extrapolated from normal stem cell biology (Burdsal et al., 1995, *Cytometry*, 21, 145-152), are known to be biased.

Therefore, the Applicants used their recently developed approach described in the International Patent application no PCT/IB2008/054872, to isolate and enrich a subpopulation of cells showing self-renewing and tumour-initiating properties. This method lies on primary cell cultures derived from human specimen and relies on simple and robust phenotypic characteristics of tumour cells and allows a fast identification and isolation of cancer-initiating cells (CICs) (referred as FL1 cells in this method) from the non tumorigenic glioma cells (referred as FL1$^+$ cells) independently of any cell surface marker, such as CD133.

The Applicants have surprisingly found that cancer-initiating cells (CICs), such as glioma-initiating cells, (more specifically the FL1$^+$ cell population as used herein) do produce their energy, divide, and survive using the aerobic pathway (TCA cycle/oxidative phosphorylation-electron transport chain). The Applicants have also surprisingly found that the glioma-initiating cells (GICs) have a different metabolism than others glioma cells (cancer cells) from the tumour bulk, which preferentially uses the aerobic glycolysis (Warburg's effect). Indeed the Applicants made an interesting and surprising finding that FL1$^+$ cells (CICs) are enriched for NADH, for active mitochondria, and active LD. Furthermore, FL1$^+$ cells have lower levels of lactate compared to FL1$^0$ cells, suggesting that FL1$^+$ cells might preferentially used the aerobic-mitochondria pathway to produce ATP.

The method disclosed in PCT/IB2008/054872 comprises the steps of:

(a) Providing a tumour cell sample;

(b) Optionally culturing the cells provided in (a) in a culture medium;

(c) Isolating in a sub-sample the cells (FL1$^+$ cells) which present autofluorescence emission detected in the FL1 channel upon laser beam excitation at a wavelength of or about 488 nm by fluorescence activated cell sorting, from the cells provided under step (a) or (b);

(d) Isolating in another sub-sample by fluorescence activated cell sorting, the cells which are not fluorescent under step (c) (FL1$^0$ cells) and which present a slight positive shift in the fluorescence detected in the FL3 and/or FL4 channel;

(e) Excluding dead cells from each of the isolated cell sub-sample obtained under steps (c) and (d);

(f) Pooling the cell sub-sample obtained under step (c) after treatment under step (e);

(g) Pooling the cell sub-sample obtained under step (d) after treatment under step (e).

The in vitro and in vivo phenotypic and behaviour differences between FL1$^+$ and FL1$^0$ glioma cell populations was supported by further characterization demonstrating that FL1$^+$ cells are enriched for sternness-related genes, are multipotent, can generate FL1$^0$ cells and are responsible for maintaining the long-term self-renewal capacity overtime. Because FL1$^0$ derived cultures do not yield any FL1$^+$ cell, it provides further evidence that FL1$^0$ cells are derived from the FL1$^+$ population, remain viable for several passages, but are unable to reacquire autofluorescent properties once they have switched from the FL1$^+$ toward the FL1$^0$ state. Therefore, this method and this isolated cell populations offers a reliable technique for testing agents, such as inhibitors, that may be useful in the treatment of cancers presenting of glioma initiating cells.

Figure 5:
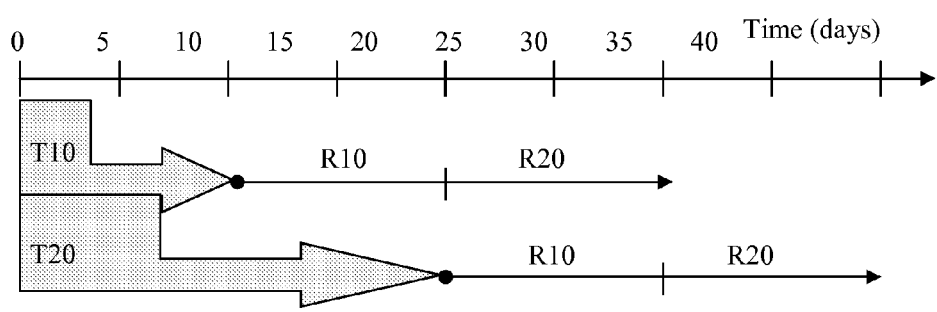
FIG. 5 shows the protocol used to test anti-cancer stem cell agents as described in Example 2. A: Experimental procedure for the treatment and recovery periods. B: Schematic viability response curve after treating CICs with an efficient anti-CSC agent (black thick line) or inefficient one (black dashed thick line). Tx refers to the treatment for a x period of time: for example 10 days (T10), 20 days (T20) and R refers to the recovery phase for a certain period of time like 10 days (R10) and 20 days (R20).
Figure 5:
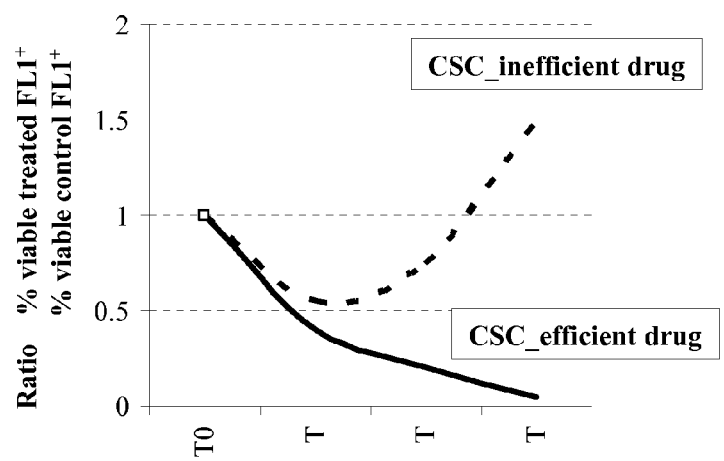
Figure 7:
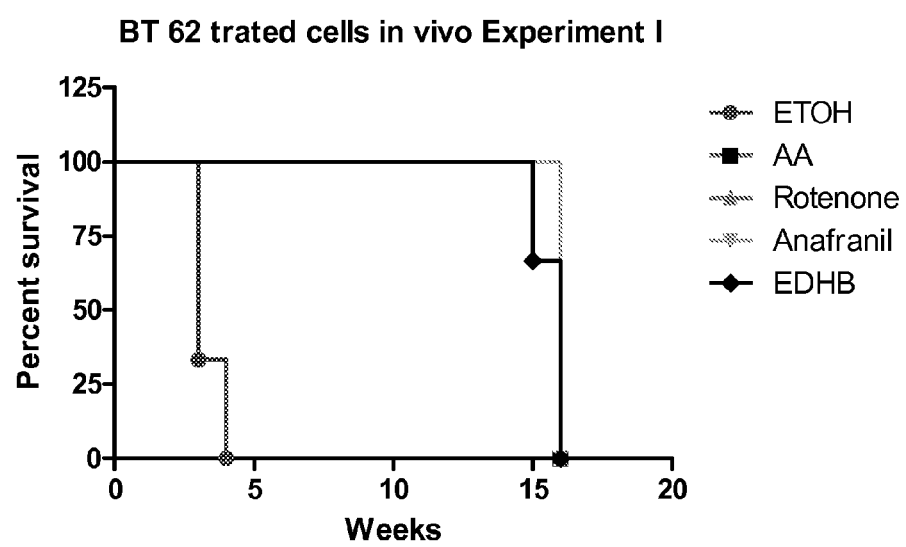
FIG. 7 shows in vivo tumorigenicity of cells treated with various inhibitors. Graphs shows the percentage of the total number of symptom-free mice following injection with primary GBM-2 cells treated with various molecules for 10 days in vitro prior implantation. Control mice had symptoms 4 weeks post-implantation and were sacrificed. Histological analyses revealed the presence of massive tumours. Mice implanted with cells pretreated with AA, Rotenone or Anafranil were alive without symptoms. Experiment was stopped 17 weeks post-implantation. Histological analyses revealed no visible tumours

Using a specific and novel in vitro recurrence assay for screening anti-GIC agent they designed (FIG. 5), the Applicants found that agent, such as inhibitor, targeting the oxidative cellular energy production process demonstrates a reliable and long-lasting efficacy to eradicate CICs. Inhibitors which prevents NADH from being converted into cellular ATP at the mitochondrial complex I or III and induces the formation of $H_2O_2$ generation might therefore be considered as novel and specific therapeutic strategy against glioma-initiating cells.

Using the above-mentioned robust technology for identifying GICs, the Applicants also developed a robust and reliable screening tool to identify specific and efficient anti-GIC agents.

By taking advantage of the Applicants' above-mentioned technology and their in vitro assay designed for testing and validating specific anti-CSC agents (anti-Cancer-Stem-Cells agents), Applicants demonstrate that blocking the production of energy generated by the aerobic pathway is sufficient for killing the whole CIC population (the killing is done by starving CICs, and not by apoptosis) Inhibitors interfering with the electron transport chain such as the one of mitochondria at the level of the complex I and III are demonstrating an exceptional capacity to kill every glioma-initiating cells in vitro and in vivo. As the inhibition of complex I and III result in large production of reactive oxygen species (ROS) and free radicals, it is likely that the CICs are also killed by the accumulation of ROS or the saturation of the detoxification system.

In contrast to other methods, which preferentially use cancer cell lines and stem cell marker like CD133 as a read-out of stemness, the Applicants' technology relies on primary cell cultures derived from human specimen and on a simple and unbiased detection of CICs independently of the use of any marker. Thus Applicants took advantage of such methodology to design and develop an in vitro recurrence assay to screen and validate potential therapeutic agents for eradicating cancer stem cells in glioma. CICs, primary glioma cells and normal brain cells are exposed to an agent, such as an inhibitor, for a maximum of 20 days, preferably 10 or 20 days (Treatment: T) prior being transferred back into the recovery phase (Recovery: R) without any agent, such as inhibitor. The novelties here reside on the read-out of stemness used for testing the efficiency of any drug and on the possibility to identify specific anti-CSC agent.

Basically, any agent or inhibitor would be considered as an efficient anti-CSC agent if it fulfils the following criteria:
1) a viability of GICs (FL1$^+$ cells) decreases for more than 50% during the exposure to said agent or inhibitor during a maximum of 20 days,
2) a recovery of GICs (FL1$^+$ cells) is less than 0.2 fold during the recovery phase of a maximum of 20 days, and
3) the viability of normal brain cells is sustainable and recoverable during and after the exposure to the said agent or inhibitor.

Preferably said agent or inhibitor is inhibitor of the activity of the electron transport chains and/or the mitochondrial TCA cycle.

As a proof of concept and validation of the Applicants' in vitro recurrence assay, the effect of γ-irradiation and temozolomide, the principal cytotoxic agent currently used for GBM were tested. In contrast to FBS-cultured glioma cells, ~40% of FL1$^+$ cells are resistant to a 25Gy irradiation, survive and therefore recover within 30 days post-genotoxic stress, confirming that radiation mostly do not target the GICs subpopulation but rather the rapidly dividing cells from the bulk. The methylation status of the MGMT promoter in gliomasphere cells was first tested as described in Hegi et al, N Engl J Med, 2005, 352 (10) 997-1003, predicting that gliomasphere cells should be sensitive to temozolomide. However, even after 25 μM temozolomide for up to 20 days, which is 5 times more the dose used in clinics, 30% of FL1$^+$ cells were still viable and able to recover within 20 days (0.2<R<1).

GBM are by definition highly heterogeneous tumours from a phenotypical and molecular point of view. Amongst signalling pathways that are differentially activated or silenced, the Epidermal Growth Factor receptor (EGFR) signalling cascade is amplified/overexpressed in ~60% of GBM and the PI3K/AKT/PTEN signalling cascade shows alterations in PTEN expression in ~65% of GBM. Similarly, loss of PTEN seems associated with a poor prognosis and radiation resistance. Long term treatment with Erlotinib at 5 μM is inducing cell death in more than 50% of FL1$^+$ cells only in 2/6 GBM independently of the EGFR status, thus confirming that the amplification of the EGFR gene doesn't correlate with the responsiveness to EGFR kinase inhibitors such as Gefitinib or Erlotinib. Furthermore, all gliomasphere cultures were able to recover from the treatment within 10 days, suggesting that blocking the EGFR signalling pathway at the level of the receptor is inefficient.

Major developmental pathways such as Notch, SHH-Gli and WNT, mTOR have been implicated in several human tumours in general including gliomas, but only rare studies have systematically addressed their role in human cancer stem cells. More specifically, blocking the activity of the SHH-Gli using cyclopamine or the activity of the NOTCH signalling pathway using the γ-Secretase inhibitor DAPT or reduces tumour-growth by potentially affecting proliferation and self-renewal of the cancer-initiating cell population. Similar, but not identical, inhibition of mTOR using temsirolimus or targeting developmental pathways like SHH-Gli or NOTCH using 5 uM cyclopamine or 5 μM DAPT respectively give rise to a decrease of the number of viable FL1$^+$ cells. But again, as residual CICs were observed even after 20 days treatment and results into a quick recovery of the CIC population, those drugs were considered as inefficient.

Based on the number of active mitochondria, the contents of metabolite and the effect of inhibitors of the anaerobic energy production pathway, FL1$^+$ cells are likely to preferentially produce their energy using the aerobic pathway in contrast to FL1$^0$ cells. Therefore, the Applicants developed the concept that any agent harbouring an efficient capacity to inhibit the mitochondrial activity should impair the energy production within CICs, which in turn is likely to kill CICs. This concept was tested by using the in vitro recurrence assay of the invention, and screened for inhibitors of the electron transport chain (like rotenone, antimycinA, anafranil) and proton pump (oligomycin A/B). Exposure to 5 μM Rotenone or Antimycin A or Anafranil (clomipramine) or Oligomycin A/B along 20 days kills all FL1$^+$ cell. As regards to the development of treatment and design of therapeutic strategies, the Applicants shortened the exposure to agents inhibiting the aerobic pathway and observed that 10 days-treatment is even sufficient to kill the whole reservoir of CICs. To test the specificity of such inhibitor towards CICs, normal brains cells and primary glioma cells (FBS cultures) were exposed to the above mentioned mitochondrial agents for 10 days. Normal brain cells and primary glioma cells were also found sensitive to oligomycinA/B, indicating that blocking the activity of the complex IV of the mitochondria might not be appropriate as it does affect the viability of normal brain cells. Though slightly affecting growth and proliferation, exposure to Antimycin A or Anafranil, and to a lesser extend to Rotenone allows normal brain cells to survive, and therefore open better perspectives as therapeutic agents. Interestingly, primary glioma cells cultured in FBS were resistant to such agents, further confirming the observation that cells from tumour bulk harbour a different metabolism than CICs do.

The present invention provides an inhibitor of the activity of the electron transport chains and/or the mitochondrial TCA cycle in glioma-initiating cells (GICs) for use in a method for preventing and/or treating tumours presenting glioma-initiating cells (GICs) in a subject who has undergone a prior removal of a tumour glioma bulk, wherein said inhibitor fulfils the following criteria:
1) a viability of GICs decreases for more than 50% during the exposure to said inhibitor of the activity of the electron transport chains and/or the mitochondrial TCA cycle during a maximum of 20 days,
2) a recovery of GICs is less than 0.2 fold during the recovery phase of a maximum of 20 days, and
3) the viability of normal brain cells is sustainable and recoverable during and after the exposure to the said inhibitor of the activity of the electron transport chains and/or the mitochondrial TCA cycle.
and whereby, said inhibitor of the activity of the electron transport chains and/or the mitochondrial TCA cycle blocks the production of energy by GICs.

Preferably said removal of a tumour glioma bulk is segmental resection of a tumour glioma bulk.

Preferably said inhibitor of the activity of the electron transport chains and/or the mitochondrial TCA cycle in glioma-initiating cells (GICs) is administered at the dosage corresponding up to 10 times $IC_2$ dose. Most preferably said $IC_2$ dose is a range of 0.157 to 0.315 mg/kg.

The tumours presenting glioma initiating cells are preferably selected from the group comprising gliomas, schwanommas, metastasis to the brain, meningiomas, ependymomas, astrocytomas, oligodendrogliomas, oligoastrocytomas, recurrent cancers and a metastatic cancers.

The term "sample" comprises a tissue or fluid sample from any source such as a tissue or fluid sample from a patient (such as a mammalian patient, more specifically a human patient) suffering from a cancer, having a recurrent cancer or suspect to suffer from a cancer such as for example human gliomas, schwanommas, metastasis to the brain, meningiomas, astrocytomas, oligodendrogliomas, oligoastrocytomas and ependymomas. In another embodiment, the sample comprises a tissue or fluid sample from any source such as a tissue or fluid sample from a patient (such as a mammalian patient, more specifically a human patient) suffering from a metastatic cancer or suspect to suffer from a cancer such as for example metastasis to the brain from melanoma, breast cancer, colon cancer, lung cancer.

The term "cancer stem cell sample" means a sample selected from a gliomasphere culture (cultured as described in the examples) containing a mixture of $FL1^+$ and $FL1^0$ cells according to the invention or a sample containing two isolated $FL1^+$ or $FL1^0$ cell populations wherein cells are isolated by a method according to the invention.

The term "tumour cell sample" comprises cell samples freshly dissociated from a tumour sample or cell samples where the cells have been cultured after dissociation from a tumour sample, like for example gliomasphere cultures such as cultured in stem cell medium and the like, adherent cell cultures such as cultured in serum rich medium and the like and differentiated cell cultures such as cultured in differentiation culture medium and the like.

As herein used, the term "tumour" (or tumor) refers to a neoplasm or a solid lesion formed by an abnormal growth of cells. A tumour can be benign, pre-malignant, or malignant. Tumour can be related to the central and peripheral nervous system, metastasis to the brain and lung metastasis, acute myeloid leukemias (AML), breast, colon and ovarian tumours. Further, the term tumour comprises also tumours such as gliomas, schwanommas, meningiomas, ependymomas, astrocytomas, oligodendrogliomas, oligoastrocytomas, melanoma.

The term "stem cell medium and the like" includes medium where cancer stem cells (also called gliomaspheres) derived from freshly dissociated tissue sample are expanded. For example, neural stem cell culture medium includes DMEM-F12-Ham's (Gibco) supplemented with Penicillin-streptomycin at 1/1,000 (Gibco), B27 (1/50 Gibco) or BIT9500 (20% Stem cell Technologies), hepes 30 mM (Sigma-Aldrich), human recombinant EGF (20 ng/ml Invitrogen) and basic FGF-2 (20 ng/ml Invitrogen)).

The term "serum rich medium and the like" includes medium where adherent cultures derived from freshly dissociated tissue sample are expanded (e.g. FBS 10%, DMEM-F12-Ham's (Gibco) supplemented with Penicillin-streptomycin at 1/1,000 (Gibco)).

The term "differentiation culture medium and the like" includes medium where cancer stem cells are plated for analysing their multipotency capacities (e.g. plates coated with a mixture of poly-L ornithine and Laminin (sigma) diluted 1:100 in $H_2O$ for O/N at 37° C. Cells are dissociated and plated at a density of cell/μl in DMEM-F12-Ham's (Gibco) supplemented with Penicillin-streptomycin at 1/1,000 (Gibco), B27 (1/50 Gibco) or BIT9500 (20% Stemcell Technologies), Hepes 30 mM (sigma-aldrich).

The term "FL1 channel" is the longitudinal detection channel of fluorescence such as described in *Practical Flow Cytometry*, Shapiro et al., 4$^{th}$ Edition, 2003, Wiley & Sons, Inc. Typically, for an excitation wavelength of 488 nm, the autofluorescence detection occurs in FL1 channel at a wavelength of or about 520 nm.

The term "FL3 channel" is the side detection (45°) channel of fluorescence such as described in *Practical Flow Cytometry*, Shapiro et al., 4$^{th}$ Edition, 2003, Wiley & Sons, Inc. Typically, for an excitation wavelength of 488 nm, the fluorescence detection occurs in FL3 channel at a wavelength >630 nm.

The term "FL4 channel" is the side detection channel of fluorescence such as described in *Practical Flow Cytometry*, Shapiro et al, 4$^{th}$ Edition, 2003, Wiley & Sons, Inc. Typically, for an excitation wavelength of or about 632 nm or of or about 546 nm, the fluorescence detection occurs in FL4 channel at a wavelength >630 nm.

The term "normal brain cells" refers to healthy brain cells having normal biological functions and not suffering from any disease or disorder such as tumour. The term "viability of normal brain cells is sustainable and recoverable" means that the normal brain cells maintains its normal biological function and is not impaired during and after the exposure to the inhibitors of the invention.

The term "$FL1^+$ cells" or "FL1-H cells" or "GICs" or "CICs" refers to cells that are sorted by fluorescence activating cell sorting through a method according to the invention, notably by selectively detecting and sorting cells which present a specific morphology (high FSC and low/middle SSC) and autofluorescence emission detected in the FL1 channel upon laser beam excitation into a cell sub-sample. This sub-sample consists in a cell sub-population presenting such autofluorescence emission detected in the FL1 channel is detected upon excitation at a wavelength of 488 nm (for example a blue laser beam, e.g. Argon) at a wavelength around 520 nm. More specifically, the FL1 autofluorescence can be detected in the FL1 channel with a dichroïc mirror at 530 nm+/−15, and more tightly with a dichroïc mirror at 515 nm+/−5, confirming the specificity of the FL1 autofluorescence emission spectrum.

The term "FL1⁰ cells" or "non FL1-H cells" or "non-autofluorescent cells" refers to cells that are sorted by fluorescence activating cell sorting through a method according to the invention, notably by selectively detecting and sorting cells which present a specific morphology (low/middle FSC and middle/high SSC), are not fluorescent in the FL1 channel and present a slight positive shift in the fluorescence detected in the FL1 or FL4 channel.

The term "FL1⁻ cells" or "primary glioma cells" or "FBS cultured glioma cells" refers to cells that are cultured in 10% FBS media, are attaching, are not sorted by fluorescence activating cell sorting through the method according to the invention. These cells which present a specific morphology (middle FSC and high SSC), high cytoplamic/nuclear ratio (>1), and are not fluorescent in the FL1 channel neither in the FL1 or FL4 channel.

The term "high FSC" or "high FSC-H" or "high FSC-A" means Forward Scatter and corresponds to the particle size and velocity measuring (cell diameter between 5-7 μm).

The term "low/middle FSC" or "low/middle FSC-H" or "low/middle FSC-A" means Forward Size Scatter and corresponds to the size of the cell (cell diameter <5-7 μm).

The term "middle/high SSC" or "middle/high SSC-H" or "middle/high SSC-A" means Side or Orthogonal Scatter and corresponds to cell complexity or granularity (cells with large cytoplasm and granular).

The term "low/middle SSC" or "low/middle SSC-H" or "low/middle SSC-A" means Side or Orthogonal Scatter and corresponds to cell complexity or granularity (cells with agranular and confined cytoplasm around nucleus).

Typically, FL1⁺ or FL1-H cells combined a "high FSC" or "high FSC-H" or "high FSC-A" with "low/middle SSC" or "low/middle SSC-H" or "low/middle SSC-A", and have therefore a nuclear/cytoplasmic diameter ratio >1.

Typically, FL1⁰ or non-FL1-H cells combined a "low/middle FSC" or "low/middle FSC-H" or "low/middle FSC-A" with "middle/high SSC" or "middle/high SSC-H" or "middle/high SSC-A", and have therefore a nuclear/cytoplasmic ratio <1.

The term "stem cell culture medium" is a medium suitable for the culture of stem cells. Typically, a stem cell culture medium includes for example mitogens (basic FGF-2, EGF) and supplement free-media (B27 or BIT9500).

The term "spherogenicity" comprises the capacity of a single stem cell to divide symmetrically or asymmetrically to form a clone. This clone is called sphere, and more precisely, it is called a gliomasphere when the sphere derived from a glioma tumor. This capacity can be measured by clonal assay also called self-renewal assay such as described in PCT/IB2008/054872. Self-renewal assay does measure the ability of a single cell to form a clone, but not all clones do form sphere. Only stem cell or early progenitor in normal development or certain cancer type shows this spherogenic potential, and this specificity exists in neural and glioma stem cells.

The term "multipotency" comprises the capacity of the cells to differentiate into several cell types, e.g for cells from the central nervous system mutipotency refers to the capacity to differentiate into cells such as GFAP (astrocytes), NESTIN (neural progenitors), TUJ1 (neurons).

The term "recovery phase" comprises the transfer of FL1⁺ and FL1⁰ cells back into the stem cell media after treatment.

The term "recurrence" means the ability of a cancer stem cell to survive, to maintain its intrinsic properties (e.g. autofluorescence in FL1 channel, spherogenicity), its division ability and optionally to maintain further properties (e.g. differentiation ability as measured by expression of differentiation markers, stemness properties as measured by expression of sternness markers and metabolic properties such as measured by the activity and ratio NAD/NADPH+ enzymes using an oxido-reduction colorimetric assay (MTS) after treatment by an agent. Measurement of recurrence is performed by a screening assay according to the invention and comprises the analyses of the presence and proportion of FL1⁺ and FL1⁰ cells after the treatment such as summarized on FIG. 5. The recurrence level will be evaluated of the basis of the proportion of surviving cancer stem cell after treatment during the recovery period and on the length of the recovery period during which no recurrence of cancer stem cell is observed.

The term "effective amount" as used herein refers to an amount of at least one compound or a pharmaceutical formulation thereof according to the invention that elicits the biological or medicinal response in a tissue, system, animal or human that is being sought. In one embodiment, the effective amount is a "therapeutically effective amount" for the alleviation of the symptoms of the disease or condition being treated. The term also includes herein the amount of active compound sufficient to reduce the progression of the disease, notably to reduce or inhibit the recurrence process (e.g. impede the recurrence to occur or decrease the recurrence process frequency or extend) of and/or to lead to and thereby elicit the response being sought (i.e. an "inhibition effective amount"). In a particular embodiment, the inhibitors, methods and uses according to the invention are able to decrease or even eradicate the FL1⁺ cell population which are at the origin of the tumour, tumour growth, recurrence and metastasis.

The term "efficacy" of a treatment according to the invention can be measured based on changes in the course of disease in response to a use or a method according to the invention. For example, the efficacy of a treatment according to the invention relies on two criteria which are:
 the capacity to kill FL1⁺ cells as measured by a reduction of at least 50% of the viable FL1⁺ cells after 10 or 20 days.
 the absence of recovering FL1⁺ cells (r<0.2) as measured by the number of viable FL1 cells up to a minimum of 20 days after treatment.

The efficacy of a treatment according to the invention can be measured by an amelioration of patient's condition and a positive influence of the treatment according to the invention on the patient.

The term "ability to inhibit cancer stem cells recurrence" refers to the property of an agent which is able to decrease the number of cancer stem cells in a cancer stem cell sample after treatment and after observation of a recovery period after this treatment. Preferably, the ability to inhibit cancer stem cells recurrence is the ability of an agent to eliminate cancer stem cells from a cancer stem cell sample and to avoid the recurrence of those cells after the observation of a recovery period.

The term "antitumour agent" or "therapeutic agent" or "agent" as used herein interchangeably, comprises molecules or compounds susceptible to have a therapeutic activity in a tumour, e.g. effective in the treatment of a tumour such as in decreasing or abolishing tumour growth, in preventing, decreasing or abolishing the cancer recurrence. It comprises agents that are known for their therapeutic activity in a cancer or agents which are investigated for their ability to have a therapeutic activity in a cancer. The term "antitumour agent" or "therapeutic agent" or "agent" also includes any molecules (e.g. chemical, biological) or any external/environmental factor (e.g. mechanical, radiation).

As used herein, "treatment" and "treating" and the like generally mean obtaining a desired pharmacological and physiological effect. The effect may be prophylactic in terms of preventing or partially preventing a disease, such as cancer (glioma), symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease, such as cancer (glioma) from occurring in a subject, who either has already undergone a treatment, such as for example surgery (resection or segmental resection), radiotherapy and/or chemotherapy, or who may be predisposed to the disease but has not yet been diagnosed as having it; (b) inhibiting the disease, such as cancer (glioma), i.e., arresting its development; or relieving the disease, i.e., causing regression of the disease and/or its symptoms or conditions.

The term "inhibitor" used in the context of the invention is defined as a molecule that completely or partially the activity of biological molecule.

The term "mitochondrial activity inhibitor" is defined as an inhibitor of the oxidative cellular energy production process, typically an inhibitor of the aerobic cell metabolism. An oxidative cellular energy production process inhibitor includes an inhibitor of the cellular tricarboxylic acid (TCA) or citric acid cycle (chemical conversion of carbohydrates, fats and proteins into carbon dioxide and water to generate a form of usable energy) or an inhibitor of the cellular oxidative (aerobic) glycolysis (metabolism of glucose to pyruvate in the cell cytoplasm) or of the oxidative phosphorylation of glycolysis substrate (pyruvate). Typically, a mitochondrial activity inhibitor is an agent which exhibits a capacity to block the electron transport chain or oxidative phosphorylation, leading to the production of Reactive Oxygen Species (ROS) in an in vitro and in vivo recurrence assays.

As used herein, the inhibitor of the activity of electron transport chains can be for example diphenyleneiodonium chloride (DPI) or derivatives thereof. DPI binds strongly to flavoproteins and is thus a powerful and specific inhibitor of several important enzymes, including nitric oxide synthase (NOS), NADPH-ubiquinone oxidoreductase, NADPH oxidases and NADPH cytochrome P450 oxidoreductase.

Preferably the inhibitor of the activity of the electron transport chains and/or the mitochondrial TCA cycle is Diphenyleneiodonium chloride (DPI) and derivatives thereof.

Further preferably the inhibitor of the activity of the electron transport chains and/or the mitochondrial TCA cycle is inhibitor of the activity of the Complex (I) and/or Complex (III) of the mitochondrial electron transport chain.

The term "inhibitor of the activity of the Complex (I) of the mitochondrial electron transport chain" includes agents that inhibit the activity of complex I of the mitochondria. For example, inhibitors of the oxidative phosphorylation complex (I) include agents that bind complex I of the mitochondria at the binding site of NADH deshydrogenase (Hogan & Singer, 1967, *Biochem. Biophys. Res. Commun.*, 27 (3): 356-60) such as rotenone, which is a known pesticide and its derivatives. Rotenone derivatives include arylazidoamorphigenin, amorphispironone, tephrosin, amorphigenin, 12a-hydroxyamorphigenin, 12a-hydroxydalpanol] and 6'-O-D-glucopyranosyldalpanol.

The term "inhibitor of the activity of Complex (III) of the mitochondrial electron transport chain" includes agents that inhibit the activity of complex III of the mitochondria. For example, inhibitors of the oxidative phosphorylation complex (III) include agents that inhibit the catalytic activity of complex III such as Antimycin A, a known antifungal, and its derivatives. Antimycin A derivatives include myxothiazol, tridecyl analog of stigmatellin (Hu et al., 2008, *Tetrahedron letters*, 49 (35): 5192-5195). Other examples of inhibitors of the oxidative phosphorylation complex (III) include any dibenzepine derivatives, which are known antidepressants, such as clomipramine, a dual serotonin-noradrenaline reuptake inhibitor (Anafranil®) or its derivatives and analogues such as imipramine and chlorpromazine. Imipramine and its hydrochloride salt are disclosed in U.S. Pat. No. 2,554,736 and its pamoate salt is in U.S. Pat. No. 3,326,896. Imipramine and its salts are orally active dibenzazepine tricyclic antidepressant. Further examples of inhibitors of the oxidative phosphorylation complex (III) are Licochalcone A, Ascochlorin and Strobilirubin B.

Dual serotonin-noradrenaline re-uptake inhibitors (DSN-RIs), which inhibit the reuptake of both serotonin and norepinephrine include venlafaxine (Effexor®), venlafaxine metabolite O-desmethylvenlafaxine, clomipramine (Anafranil®), clomipramine metabolite desmethylclomipramine, duloxetine (Cymbalta®), milnacipran and imipramine (Tofranil® or Janimine®).

Their chemical names, trade names, structures, therapeutic and pharmacologic information, and therapeutic category can be found in the literature such as, for example, in the Merck Index, 9th Edition 1976, Goodman & Gilman, The Pharmacological Basis of Therapeutics, 9th Edition 1996, and the Physician's Desk Reference 2004.

Typically according to the present invention, an inhibitor inhibits either the activity of the mitochondrial oxidative phosphorylation complex (I) or the activity of the mitochondrial oxidative phosphorylation complex (III).

However, some inhibitors such as Stigmatellin, Myxothiazol, Piericidin or derivatives and analogues thereof, can simultaneously inhibit the activity of the mitochondrial oxidative phosphorylation of both complexes (I) and (III). The above-mentioned dual inhibitors can be more potent inhibitors and therefore more potent anti-GICs agents requiring lower concentrations.

Table 1 lists classic agents used in radiotherapy and chemotherapy or in clinical trials, the references in the literature and the dose used for the in vitro recurrence assay.

Tables 2-3 list agents targeting the aerobic/anaerobic pathways, the references in the literature and the dose used for the in vitro recurrence assay.

Preferably the inhibitor of activity of the Complex (I) and/or Complex (III) of the mitochondrial electron transport chain is selected from the group comprising Rotenone, Antimycin A, Imipramine, Clomipramine, Myxothiazole, Stigmatellin, Strobilurin b, Licochalcon A, Ascochlorin, Piericidin, and/or combinations thereof, and/or derivatives thereof, and/or pharmaceutically acceptable salts thereof.

For example, said combination of the inhibitors of activity of the Complex (I) and Complex (III) of the mitochondrial electron transport chain consists in combining Rotenone with Antimycin A or Rotenone with Clomipramine.

Most preferably, the inhibitor of activity of the Complex (I) and/or Complex (III) of the mitochondrial electron transport chain is selected from the group comprising Myxothiazole, Stigmatellin, Piericidin, and/or derivatives thereof, and/or pharmaceutically acceptable salts thereof.

The term "inhibitor of the activity of the mitochondrial TCA cycle" includes compounds which are usually determined by substrate availability, endogeneous and/or exogeneous of end products. The inhibitors of the activity of the mitochondrial TCA cycle are for example NADH and ATP, citrate, Acetyl-CoA, calcium inhibits key enzymes of the TCA such as isocitrate dehydrogenase, α-ketoglutarate dehydrogenase, and also citrate synthase. Preferably according to the present invention, the activity of mitochondrial TCA cycle can be inhibited indirectly with the inhibitors of electron transport chains, such as inhibitors of Complex (I) and Complex (III) of the mitochondrial electron transport chain selected from the group comprising Rotenone, Antimycin A, Imipramine, Chlomipramine, Myxothiazole, Stigmatellin, Strobilurin b, Licochalcon A, Ascochlorin, Piericidin, and/or combinations thereof, and/or derivatives thereof, and/or pharmaceutically acceptable salts thereof.

TABLE 1

| Agent | Target | Dose range used in the litterature | Dose range tested | Dose used |
| --- | --- | --- | --- | --- |
| γ irradiation | Create double strand breaks into DNA | 2-5*3 Gy (Chang et al, 2009; Bao et al, 2006) | 5-25 Gy | 25 Gy |
| Temozolomide | Alkylating agent. It acts mainly by methylating the O6 position of Guanine. Its benefits depend on the methylation state of the MGMT promoter | 5-500 μM (Beier et al, 2008; Clément et al, 2007) | 10-500 μM | 25 μM |
| Erlotinib | EGFR signaling pathway inhibitor. | 0.5-5 μM (Griffero et al, 2009) | 1-50 μM | 5 μM |
| Temsirolimus | mTOR signaling pathway inhibitor | 0.1 pM-10 μM (Goudar et al, 2005; Georger et al, 2001) | 10-1000 pM | 1 nM |
| Cyclopamine | Inactivation of SHH-Gli signaling pathway activity | 1-10 μM (Clément et al, 2007; Bar et al, 2007) | 1-50 μM | 5 μM |
| DAPT | Gamma-secretase inhibitor. Inactivation of NOTCH signaling pathway activity. | 5-25 μM (Gal et al, 2007; Fan et al, 2006) | 1-50 μM | 25 μM |

TABLE 2

| Agent | Target | Dose range used in the litterature | Dose range tested | Dose used |
| --- | --- | --- | --- | --- |
| Rotenone | Mitochondrial inhibitor. It inhibits the transfer of electrons from iron-sulfur centers in complex I to ubiquinone | 0.3-50 μM (Griguer et al, 2008; Chen et al, 2007; Kim et al, 2007) | 1-50 μM | 5 μM |
| Antimycin A | Mitochondrial inhibitor. It blocks the flow of electrons from semiquinone to ubiquinone in the Q-cycle of complex III | 20-500 μM (Yang et al, 2005 ; Jeong et al, 2003; Lomneth et al, 1989, Kim et al, 2007) | 1-50 μM | 5 μM |
| Imipramine | Clomipramine analog, Tricyclic/antidepressant agent. Its function as an inhibitor of the mitochondrial complex III as not be proven | 1-1000 μM (Yang et al, 2005; Jeong et al, 2003; Lomneth et al, 1989, Kim et al, 2007) | 1-100 μM | 10 μM |
| Clomipramine (also named Anafranil) | Tricyclic/antidepressant agent and Mitochondrial inhibitor. It blocks the flow of electrons from semiquinone to ubiquinone in the Q-cycle of complex III | 1-1000 μM (Bilir et al., 2008; Daley et al., 2005; Pilkington et al., 2008) | 1-50 μM | 10 μM |
| Oligomycin A/B | It inhibits the complex IV of the mitochondria by blocking the ATP synthase proton pump | 0.1 μM-1 mM (Balestri et al, 2007; Katayama et al, 2007; Kim et al, 2007) | 1-50 μM | 5 μM |

TABLE 3

| Agent | Target | Dose range used in the litterature (if studied) | Dose range tested | Dose used |
| --- | --- | --- | --- | --- |
| Myxothiazol | Mitochondrial inhibitor of the complex I and III | Nd (Von Jagow and A link, 1986; Degli Esposti et al., 1993) | 0.1-50 μM | nd |
| Stigmatellin | Mitochondrial inhibitor of the complex I and III | Nd (Von Jagow and A link, 1986; Kessl et al., 2003; Gurung et al., 2008; Degli Esposti et al., 1993) | 0.1-50 μM | nd |
| Strobilurin b | inhibitor of the mitochondrial complex III | Nd (Von Jagow and A link, 1986) | 1-50 μM | 5 μM |
| Licochalcon A | inhibitor of the mitochondrial complex III | Nd (Von Jagow and A link, 1986; Mi. Ichi et al., 2005) | 1-100 μM | 1 μM |
| Ascochlorin | inhibitor of the mitochondrial complex III | Vnd (on Jagow and A link, 1986) | 0.1-10 μM | 1 μM |
| Dichloro-actetate (DCA) | It pushes cells toward the aerobic pathway, and therefore activates of the oxidative pathway | (Michelakis et al., 2008) | 100 μM-10 mM | 500 μM |
| Diphenyleneiodonium chloride (DPI) | General Inhibitor of electron transporter of the mitochondria, of NO synthase, NAPDH oxidase | O'Donnel et al., 1993; Wang et al., 1993 | 1-50 μM | 5 μM |
| Oxamate | inhibition of cytosolic LDH3-5 | 10 mM (Lemire et al, 2008) | 1-50 mM | 10 mM |

In a further embodiment, the present invention provides a combination of different inhibitors of the invention, which provides a synergic and/or cumulative effect. For example combination of inhibitors of the Complex (I) and the Complex (III) of the mitochondrial electron transport chain, such as combination of rotenone and antimycin or rotenone and anafranil, can be performed in order to optimize the efficacy of a treatment to eradicate the whole GIC reservoir. As previously observed such combination of inhibitors would allow to decrease the individual doses of each inhibitors, which can act synergistically or cumulatively to kill GICs. Example of such combination and synergism: Clement et al, 2007 and Stecca et al, 2007.

The term "ROS producing agent" is an agent that is able to induce an increase in the levels of reactive oxygen species (ROS) and free radicals in a cell. Typically, such agents include cinnalmadehyde, hydrogen peroxide, actinomycin D and camptotecin.

As herein used, an "electron transport chain" (ETC) couples a chemical reaction between an electron donor (such as NADH) and an electron acceptor (such as $O_2$) to the transfer of $H^+$ ions across a membrane, through a set of mediating biochemical reactions. These $H^+$ ions are used to produce adenosine triphosphate (ATP), the main energy intermediate in living organisms, as they move back across the membrane. For example most eukaryotic cells, that use oxygen as part of cellular respiration, contain mitochondria, which produce ATP from products of the Krebs cycle, fatty acid oxidation, and amino acid oxidation. At the mitochondrial inner membrane, electrons from NADH and succinate pass through the electron transport chain to oxygen, which is reduced to water. In mitochondria, four membrane-bound Complexes have been identified to be involved in the electron transport chain. Each Complex is an extremely complex transmembrane structure that is embedded in the inner membrane. These four Complexes are Complex (I) (NADH dehydrogenase, also called NADH:ubiquinone oxidoreductase), Complex (II) (succinate dehydrogenase), Complex (III) (cytochrome $bc_1$ complex), and Complex (IV) (cytochrome c oxidase).

The electron transport chains are also major sites of premature electron leakage to oxygen, thus being major sites of superoxide production and drivers of oxidative stress.

As herein used, the "TCA cycle" (tricarboxylic acid cycle), also known as citric acid cycle, is a series of enzyme-catalyzed chemical reactions, which is of great importance in all living cells that use oxygen as part of cellular respiration. In eukaryotic cells, the TCA cycle occurs in the matrix of the mitochondria.

The term "removal of a tumour glioma bulk" refers to any removal, ablation or resection of a tumour glioma bulk from a subject. The removal can be chemical, radiation or surgical. Preferably said removal is surgical, such as ablation or resection. Resection can be "segmental resection" (or segmentectomy), a surgical procedure to remove part of an organ or gland from a subject. It may also be used to remove a tumour and normal tissue around it.

The term "blocks the production of energy by GICs" refers to inhibiting the metabolic reactions and processes that take place in glioma-initiating cells (GICs) to convert biochemical energy from nutrients into adenosine triphosphate (ATP). Usually blocking the product of energy means that the cells are starving.

The term "recurrent cancer" or "recurrent tumour", refers to a cancer, for example glioma, that has recurred (come back), usually after a period of time during which the cancer could not be detected. The cancer may come back to the same place as the original (primary) tumour or to another place in the body of a subject.

The term "debulking agent" includes any molecule (e.g. chemical, biological) or any external/environmental agent (e.g. γ-irradiation) or traditional surgery that would allow killing cancer cells from the tumour bulk (e.g. $FL1^\circ$ and $FL1^-$ cells).

The term "standard radiotherapy" refers to the use of ionizing radiation as part of cancer treatment to control malignant cells. Preferably the ionizing radiation is γ-irradiation. It is also common to combine radiotherapy with surgery, chemotherapy, hormone therapy, or combinations thereof. Most common cancer types can be usually treated with radiotherapy. The precise treatment intent (curative, adjuvant, neoadjuvant or palliative) will depend on the tumour type, location, and stage, as well as the general health of the subject in need thereof.

The term "standard chemotherapy" generally refers to a treatment of a cancer using specific chemotherapeutic/chemical agents. A chemotherapeutic agent refers to a pharmaceutical agent generally used for treating cancer. The chemotherapeutic agents for treating cancer include, for example, cisplatin, carboplatin, etoposide, vincristine, cyclophosphamide, doxorubicin, ifosfamide, paclitaxel, gemcitabine, docetaxel, and irinotecan and platinum-based anti-cancer agents, including cisplatin and carboplatin. Other chemotherapy classes comprise tyrosine kinase inhibitors such as gefitinib, imatinib; farnesyl transferase inhibitors including lonafarnib; inhibitors of mammalian targets of rapamycin (mTOR) such as evereolimus; angiogenesis inhibitors including bevacizumab, sunitibid and cilengitide; inhibitors of PKC; PI3K and AKT. More specifically, the chemotherapeutic agents of the present invention include alkylating agents such as temozolomide or carmustine. According to the present invention, the preferred agent for the standard chemotherapy are temozolomide and bevacizumab.

The standard radiotherapy and chemotherapy of glioma can be also the concomitant chemo-radiotherapy. The term "concomitant chemo-radiotherapy" is used when these two treatments (chemotherapy and radiotherapy) are given either at the same time, or almost at the same time, for instance one after the other, or on the same day, etc. Another standard radiotherapy and chemotherapy of glioma can be combined chemo-radiotherapy of concomitant and adjuvant temozolomide and radiotherapy (TMZ/RT→TMZ) (Stupp et al., 2005, 2009).

In the method of the present invention related to preventing and/or treating tumours presenting glioma initiating cells, it is important that a subject has undergone a prior removal of a tumour glioma bulk. Indeed, depending on initial presenting symptoms (seizure, focal neurological deficit, signs of intracranial hypertension, personality alteration), specialty follow-up is organized and imagery is performed often yielding the radiological discovery of an intracranial mass. Although radiological features and patient history can raise suspicions of tumour type and aetiology, the conclusive verdict will be issued by a pathological examination following biopsy or gross resection. Thus, the removal of a tumour glioma bulk, by for example segmental resection (biopsy or gross resection), is always performed prior to the administration of a therapeutically effective amount of the inhibitor of the activity of the electron transport chains and/or the mitochondrial TCA cycle of the present invention. For example the removal of the tumour glioma bulk can be performed by standard surgery methods. This debulking step allows removing the glioma-initiating cells (up to 5-7% of the tumour glioma bulk in high grade glioma) and the rest of tumor which contains essentially tumour glioma cells, macrophages, endothelial cells (about 93-95% of the tumour glioma bulk).

In a further embodiment, the administration of a therapeutically effective amount of inhibitors of the activity of the electron transport chains and/or the mitochondrial TCA cycle of the present invention, or pharmaceutical compositions containing thereof, is performed after surgery removing tumour glioma bulk as a prophylaxis or a prevention against recurrence.

As the metabolism of glioma-initiating cells differs from the glioma bulk cells and from normal brain cells, the combination of specific agent for debulking (eradicating $FL1^o$ cells and $FL1^-$ cells) and specific inhibitor for glioma-initiating cells (eradicating $FL1^+$ cells) can be an advantageous strategy to eradicate growth and recurrence of glioma. Therefore, optionally, the standard radiotherapy and/or chemotherapy can be performed before, simultaneously or after the administration of a therapeutically effective amount of inhibitors of the activity of the electron transport chains and/or the mitochondrial TCA cycle of the present invention, or pharmaceutical compositions containing thereof. If the standard chemotherapy is performed simultaneously with the administration of a therapeutically effective amount of the inhibitors of the activity of the electron transport chains and/or the mitochondrial TCA cycle of the present invention, the chemotherapeutic agent can be administered in the same or different composition(s) and by the same or different route(s) of administration.

Preferably, the standard radiotherapy and/or chemotherapy can be performed before or after the administration of a therapeutically effective amount of the inhibitors of the activity of the electron transport chains and/or the mitochondrial TCA cycle of the present invention, or pharmaceutical compositions containing thereof.

For example the application of radiotherapy and/or chemotherapy after the administration of a therapeutically effective amount of the inhibitors of the activity of the electron transport chains and/or the mitochondrial TCA cycle of the present invention, or pharmaceutical compositions containing thereof, is supported by the fact that the Applicants observed that the phenotypical switch from tumorigenic ($FL1^+$ cells) towards a non tumorigenic state ($FL1^o$ cells) is irreversible and correlates with a commitment towards differentiation and cell death. Therefore an alternative therapeutic strategy can consist in first inducing a metabolic switch from aerobic to aerobic glycolysis in GICs so that every single $FL1^+$ cell switched into the $FL1^o$ phenotype, and second using a debulking agent (i.e. radiotherapy and/or chemotherapy), optionally in combination with neurosurgery, to eliminate the whole $FL1^o$ cell and $FL1^-$ cell populations. The application of radiotherapy and/or chemotherapy after the administration of a therapeutically effective amount of the inhibitors of the activity of the electron transport chains and/or the mitochondrial TCA cycle of the present invention, or pharmaceutical compositions containing thereof, is also supported by the fact that GICs are resistant to and recover after standard radiotherapy and/or chemotherapy (FIG. 6).

In another example, the application of standard radiotherapy and/or chemotherapy before the administration of a therapeutically effective amount of the inhibitors of the activity of the electron transport chains and/or the mitochondrial TCA cycle of the present invention, or pharmaceutical compositions containing thereof, can be useful in the treatment and/or prevention of recurrent glioma.

The present invention also provides a dosage regimen to be used in the method of preventing and/or treating tumours presenting glioma initiating cells in a subject who has undergone a prior removal of a tumour glioma bulk.

For short term dose-response, GICs are exposed to increasing dose of inhibitors for 48 hours. The viability, cell death and the recovery of GICs are then analyzed by the method described in the present invention. The dose chosen for the long term treatment (i.e. or 20 days followed by recovery) corresponds to a dose of an inhibitor which induces a two fold increase (i.e. doubles) the total number of cell death compared to the control molecule and this dose is named IC2. Contrary to the standard IC50, which correspond to the dose that induces a minimum of 50% cell death at 48 hrs), the Applicants' IC2 allows to determine a dose, which is very low, and therefore not toxic.

According to the present invention, IC2 corresponds preferably to a range of 0.157 to 0.315 mg/kg, depending on the inhibitors. The dosage regimen according to the present invention can be up to 10 times the IC2 dose, i.e. 1.57 to 3.15 mg/kg, if no sign of toxicity is observed. This dose might maximize the chances that the appropriate and sufficient dose of inhibitors passes the blood brain barrier and diffuse into the tumour site.

The dosage administered, as single or multiple doses, to a subject can vary depending upon a variety of factors, including pharmacokinetic properties, patient conditions and characteristics (sex, age, body weight, health, size), extent of symptoms, concurrent treatments, frequency of treatment and the effect desired.

The treatment can usually comprise a multiple administration of the inhibitors of the activity of the electron transport chains and/or the mitochondrial TCA cycle according to the invention or the pharmaceutical compositions comprising thereof, usually in intervals of several hours, days or weeks.

The invention provides inhibitors, pharmaceutical compositions and methods for treating a subject, who has undergone a prior removal of a tumour glioma bulk, preferably a mammalian subject, and most preferably a human patient who is suffering from a tumour presenting glioma initiating cells or recurrent tumour presenting glioma initiating cells, in particular embodiment, human gliomas, schwanommas, metastasis to the brain, meningiomas, ependymomas, a recurrent cancer, such as recurrent glioma, a metastatic cancer such as for example melanoma, breast cancer, colon cancer or lung cancer.

The present invention also provides a method of preventing and/or treating tumours presenting glioma initiating cells in a subject who has undergone a prior removal of a tumour glioma bulk, said method comprises the administration of a therapeutically effective amount of an inhibitor of the activity of the electron transport chains and/or the mitochondrial TCA cycle, wherein said inhibitor fulfils the following criteria:
1) a viability of GICs decreases for more than 50% during the exposure to said inhibitor of the activity of the electron transport chains and/or the mitochondrial TCA cycle during a maximum of 20 days,
2) a recovery of GICs is less than 0.2 fold during the recovery phase of a maximum of 20 days, and
3) the viability of normal brain cells is sustainable and recoverable during and after the exposure to the said inhibitor of the activity of the electron transport chains and/or the mitochondrial TCA cycle,
and whereby, said inhibitor of the activity of the electron transport chains and/or the mitochondrial TCA cycle blocks the production of energy by GICs.

Preferably said removal of a tumour glioma bulk is segmental resection of a tumour glioma bulk.

Preferably said therapeutically effective amount is up to 10 times $IC_2$ dose. Most preferably said $IC_2$ dose is a range of 0.157 to 0.315 mg/kg.

In an alternative embodiment, the method of preventing and/or treating tumours presenting glioma initiating cells in a subject who has undergone a prior removal of a tumour glioma bulk of the present invention can further comprises the step of treatment by standard radiotherapy and/or chemotherapy before or after the administration of a therapeutically effective amount of said inhibitor of the activity of the electron transport chains and/or the mitochondrial TCA cycle.

Preferably said inhibitor of the activity of the electron transport chains and/or the mitochondrial TCA cycle is Diphenyleneiodonium chloride (DPI) and derivatives thereof. In a further embodiment, preferably said inhibitor of the activity of the electron transport chains and/or the mitochondrial TCA cycle is inhibitor of the activity of the Complex (I) and/or Complex (III) of the mitochondrial electron transport chain.

Preferably the tumours presenting glioma initiating cells are selected from the group comprising gliomas, schwanommas, metastasis to the brain, meningiomas, ependymomas, astrocytomas, oligodendrogliomas, oligoastrocytomas, recurrent cancers and metastatic cancers.

The present invention further provides a pharmaceutical composition for preventing and/or treating tumours presenting glioma-initiating cells (GICs) in a subject who has undergone a prior removal of a tumour glioma bulk, comprising at least one inhibitor of the activity of the electron transport chains and/or the mitochondrial TCA cycle according to the present invention, and one or more pharmaceutically acceptable diluents or carriers.

Preferably the pharmaceutical composition of the present invention comprises a combination of one inhibitor of Complex (I) of the mitochondrial electron transport chain with one inhibitor of Complex (III) of the mitochondrial electron transport chain, and one or more pharmaceutically acceptable diluents or carriers.

The inhibitors of the activity of the electron transport chains and/or the mitochondrial TCA cycle according to the invention may be formulated as pharmaceutical compositions, which can contain at least one inhibitor of the activity of the electron transport chains and/or the mitochondrial TCA cycle according to the invention in any form described herein. Pharmaceutical compositions of the invention may further comprise one or more pharmaceutically acceptable diluents or carriers such as, but not limited to, alum, stabilizers, antimicrobial agents, buffers, coloring agents, flavoring agents, adjuvants, and the like.

The pharmaceutical compositions of the present invention for parenteral and enteral administrations can contain any conventional additives, such as excipients, adjuvants, binders, disintegrants, dispersing agents, lubricants, diluents, absorption enhancers, buffering agents, surfactants, solubilizing agents, preservatives, emulsifiers, isotonizers, stabilizers, solubilizers for injection, pH adjusting agents, etc.

Acceptable carriers, diluents and adjuvants which facilitates processing of the inhibitors of the invention into pharmaceutical composition which can be used pharmaceutically are non-toxic to subjects (patients) at the dosages and concentrations employed, and can include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONICS® or polyethylene glycol (PEG).

The inhibitors of the activity of the electron transport chains and/or the mitochondrial TCA cycle according to the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. Compositions according to the invention are preferably parenteral compositions.

The pharmaceutical compositions of the invention, containing at least one inhibitor of the activity of the electron transport chains and/or the mitochondrial TCA cycle, may be also liquid formulations including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavours and the like. The pharmaceutical compositions of the invention may also be formulated as a dry product for reconstitution with water or other suitable vehicle before use. Such liquid preparations may contain additives including, but not limited to, suspending agents, emulsifying agents, non-aqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in Part 5 of *Remington's Pharmaceutical Sciences*, $20^{th}$ Edition, 2000, Mack Publishing Company, Easton, Pa., which is incorporated herein by reference.

In an embodiment, subjects according to the invention are patients suffering from a cancer presenting glioma initiating cells. In a particular embodiment, the patients according to the invention suffer from human gliomas, schwanommas, metastasis to the brain, meningiomas or ependymomas. In another particular embodiment, the patients according to the invention suffer from recurrent cancers, such as recurrent glioma. In a further embodiment, the patients according to the invention suffer from metastatic cancers such as for example melanoma, breast cancer, colon cancer or lung cancer.

The inhibitors of the activity of the electron transport chains and/or the mitochondrial TCA cycle of this invention or the pharmaceutical compositions comprising thereof can be administered via various routes, such as parenteral or enteral routes. Parenteral administration comprises intravenous, intramuscular, intraarterial or intracerebral administrations. Enteral administration comprises any oral, gastric or rectal administration. Delivery methods for the composition of this invention include known delivery methods for anti-cancer drugs such as intra-venal peripheral injection, intra-tumoral injection or any type of intracranial delivery such as convection enhanced delivery (CED) (Bobo et al., 1994, *PNAS*, 91 (6), 2076-2080; Lino et al., 2009, *Curr. Opin. Cell Biol.*, 21, 311-316).

According to further embodiment of the invention, the inhibitors of the activity of the electron transport chains and/or the mitochondrial TCA cycle according to the invention and the pharmaceutical compositions comprising thereof can be administered alone or in combination with a co-agent useful in the treatment of cancer, such as substances used in standard radiotherapy and/or chemotherapy directed against solid tumours. For example a co-agent selected from debulking agents such as temozolimide or γ-irradiation.

The present invention further provides a screening method for identifying inhibitors of the activity of the electron transport chains and/or the mitochondrial TCA cycle in glioma-initiating cells (GICs), said method comprises contacting the FL1$^+$ cells, isolated from a tumour cell sample, and normal brain cells with an inhibitor to be screened, wherein said inhibitor fulfils the following criteria:
1) a viability of FL1$^+$ cells decreases for more than 50% during the exposure to said inhibitor during a maximum of 20 days,
2) a recovery of FL1$^+$ cells is less than 0.2 fold during the recovery phase of a maximum of 20 days, and
3) the viability of normal brain cells is sustainable and recoverable during and after the exposure to the said inhibitor.

The screening method of the present invention also comprises contacting primary glioma cells with said inhibitor to be screened.

The present invention also provides for a kit for screening inhibitors of the activity of the electron transport chains and/or the mitochondrial TCA cycle in glioma-initiating cells (GICs) fulfilling the following criteria:
1) a viability of FL1$^+$ cells decreases for more than 50% during the exposure to said inhibitors during a maximum of 20 days,
2) a recovery of FL1$^+$ cells is less than 0.2 fold during the recovery phase of a maximum of 20 days, and
3) the viability of normal brain cells is sustainable and recoverable during and after the exposure to the said inhibitors,
and useful in the treatment of tumours presenting glioma initiating cells, wherein said kit comprises primary CIC cultures, primary adherent glioma cells, normal cells and at least one standard inhibitor of the activity of the Complex (I) or Complex (III) of the mitochondrial electron transport chain selected from the group comprising rotenone and antimycin A.

The kit featured herein can also include an information material describing how to perform the screening for the inhibitor. The information material can also include instructions for how to determine if the tested inhibitor fulfils the criteria of the present invention. The informational material of the kit is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. Of course, the informational material can also be provided in any combination of formats.

The kit can further contain separate containers, dividers or compartments for the reagents and informational material. Containers can be appropriately labelled.

The inhibitors of the activity of the electron transport chains and/or the mitochondrial TCA cycle, uses thereof, method, and kits of the invention have the advantage to allow killing the whole population of cancer stem cells, avoiding cancer stem cell recurrence after standard cancer treatments, such as standard surgery, radiotherapy and chemotherapy. Those particular properties present the particular advantage to be useful in particular in the context of tumour prevention and/or treatment wherein they can be used in combination with a standard cancer debulking agent, enabling to kill both cancer cells, such as glioma cells and cancer-initiating cells, such as glioma-initiating cells, inhibiting cancer recurrence due to remaining cancer stem cell after standard cancer treatment.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

The foregoing description will be more fully understood with reference to the following Examples. Such Examples, are, however, exemplary of methods of practising the present invention and are not intended to limit the scope of the invention.

EXAMPLES

General Procedures and Conditions

The following examples confirm the role of aerobic energy production pathway in cancer initiating cells and the potential activity of cancer stem cell mitochondrial activity inhibitors on the treatment of cancers.

The following abbreviations refer respectively to the definitions below:

Gy (Gray), mM (millimolar), μM (micromolar), nm (nanometer), AML (acute myeloid leukemia), ATP (Adenosine triphosphate), BIT 9500 (Bovine serum albumin, Insulin, Transferring), BSA (Bovine Serum Albumin), CIC (cancer initiating cell), DAPT (N—[N-(3,5-Difluorophenacetyl-L-alanyl)]-S-phenylglycine t-Butyl Ester), DCA (dichloroacetate), DMSO (Dimethyl Sulfoxide), EGF (Epidermal Growth Factor), DMEM (Dulbecco's Modified Eagle Medium), FBS (Fetal Bovine Serum), FSC (Forward scatter), FGF-2 (fibroblast growth factor 2), GBM (Glioblastoma), GLC (glucose), LD (Lactate deshydrogenase), MGMT (O$^6$-methylguanine-DNA methyltransferase), MTS ([3-(4,5-dimethyl-2-yl)-5-(3-carboxymethoxyphenyl)-2-(4-sulfophenyl)-2H-tetrazolium, inner salt), MTS ([3-(4,5-dimethyl-2- yl)-5-(3-carboxy methoxyphenyl)-2-(4-sulfophenyl)-2H-tetrazolium, inner salt), NADH (nicotinamide adenine dinucleotide), NB (normal brain cells), OD (optical density), PFA (Para Formaldehyde), PBS (Phosphate Buffered Saline), ROS (reactive oxygen species), R (recovery), r (partial Recovery), SC (Stem Cell), SSC (Side scatter), T (treatment).

The screening method used was described in PCT/IB2008/054872, i.e. comprising the following steps:

a) Providing a cancer stem cell sample;
b) Treating the cancer stem cell sample provided under (a) with an agent;
c) Incubating the treated stem cell sample in a stem cell culture medium for an incubation period without treatment;
d) Selecting the viable cell population from the stem cell sample incubated under step (c);
e) Measuring the mean level of autofluorescence on the viable cell population isolated under step (d) by detecting, by fluorescence activated cell sorting, cells presenting autofluorescence emission in the FL1 channel upon laser beam excitation at a wavelength of or about 488 nm;
f) Isolating cells by fluorescence activated cell sorting cell which have a specific morphology (high FSC and low/middle SSC) and present autofluorescence emission in the FL1 channel upon laser beam excitation at a wavelength of or about 488 nm of the viable cell population isolated under step (d);
g) Isolating cells by fluorescence activated cell sorting which have a specific morphology (low/middle FSC and middle/high SSC), do not present autofluorescence emission in the FL1 channel under step (d) and present a slight positive shift in the cell fluorescence emission in the FL1 and/or FL4 channel upon laser beam excitation of the viable cell population isolated under step (d);
h) Calculating the percentage of autofluorescent viable cells by comparing the mean level of autofluorescence in the cancer stem cell sample provided under step (a) and the mean level of autofluorescence measured under step (e);
i) Calculating the percentage of the cell death by comparing the number of initial cells present in the cancer stem cell sample provided under step (a) and the resulting viable cell population isolated under step (d);
j) Calculating the percentage of viable FL1$^+$ cells by comparing the number of initial FL1 cells present in the cancer stem cell sample provided under step (a) and the resulting viable FL1$^+$ cell population isolated under step (f);
k) Calculating the percentage of viable FL1$^0$ cells by comparing the number of initial FL1$^0$ cells present in the cancer stem cell sample provided under step (a) and the resulting viable FL1$^0$ cell population isolated under step (g);
l) Detecting spherogenicity of the cell populations detected under steps (f) and (g).
m) Determining the activity of the agent through its ability to inhibit cancer stem cells recurrence.

The following material was used:
  6 primary CIC cell cultures produced according to the methodology described in PCT/IB2008/054872
  2 primary adherent glioma cells, referred to as cancer cells, and 2 normal brain cells were cultured in FBS media containing DMEM-F12-Glutamax, 10% Foetal Bovine Serum (FBS, Invitrogen) supplemented with 1/1000 penicillin/streptomycin.

Additional facultative parameters for testing the efficacy an agent to kill CICs (option within the screening kit) include:
  Percentage of proliferating cells (like Ki67$^+$ cells) as follows: after the treatment and/or recovery, cells were harvested, washed and fixed using PFA 4%. Cells were permeabilised using PBS1x-BSA1% with 0.1% TritonX-100 prior staining with anti-human Ki67 antibody in PBS1x-BSA1% (incubation on ice for 30 min under rotation). Cells were washed with PBS1x 2 times prior incubation with the secondary antibody diluted again in PBS1x-BSA1% (at 4° C. under rotation for 30 min). The percentage of Ki67$^+$ cells within the FL1$^+$ and FL1$^0$ cell populations was finally determined by FACS.

Expression of sternness genes by real-time PCR (such as OCT4, SOX2, NANOG, or NOTCH1) as follows: After the treatment and/or recovery, cells were harvested. Total RNAs were extracted using the RNAqueous-Micro kit (Ambion). Reverse transcription was performed using Superscript II (Invitrogen). Quantitative RT-PCR reactions were performed using the SYBER green master mix (Applied Biosystems) and samples were run on a 7900HT sequence detection system machine (Applied Biosystems). Refer to Clement, 2007, *Curr Biol*, 17, 165-172 for primer sequences.

Expression of at least one differentiation marker (TUJ1, MAP2 or GFAP) as follows: after the treatment and/or recovery, cells were harvested, washed and fixed using PFA 4%. Cells were permeabilised using PBS1x-BSA1% with 0.1% TritonX-100 prior staining with anti-human MAP2 or anti-human GFAP or anti-human TUJ1 antibody in PBS1x-BSA1% (incubation on ice for 30 min under rotation). Cells were washed with PBS1x 2 times prior incubation with the secondary antibody diluted again in PBS1x-BSA1% (at 4° C. under rotation for 30 min). The percentage of positive cells within the FL1$^+$ and FL1$^0$ cell populations was finally determined by FACS.

Tumour cell samples (for example from human source) for use in a method according to the invention under step (a) were prepared by the obtaining of a biopsy of the corresponding tumour tissue is obtained under sterile conditions using standards methods adapted to the specific cells that will be collected. Example of tumour and normal brain samples used are listed under tables 4 and 5 below:

TABLE 4

| Tumor type | Grade | Location | Gender | Age |
|---|---|---|---|---|
| O.A III-1 | Oligo-Astrocytoma grade III | Temporo-amygdala left | M | 50 |
| O.A III-1 recurrence | Oligo-Astrocytoma grade III recurrence | Temporo-amygdala left | M | 51 |
| Primary GBM-2 | Astrocytoma grade IV (glioblastoma) | Temporal left | F | 67 |
| Primary GBM-3 | Astrocytoma grade IV (glioblastoma) | Fronto-temporal left | M | 50 |
| Primary GBM-15 | Astrocytoma grade IV (glioblastoma) | Parietal right | F | 80 |
| Secondary GBM-1 | Astrocytoma grade IV (glioblastoma) | Frontal right | M | 64 |
| GSM IV-1 | Gliosarcoma grade IV | Temporal right | M | 70 |

TABLE 5

| Tissue | Origin | Location | Gender | Age |
|---|---|---|---|---|
| NB2 | Non-tumorigenic Epileptic | Frontal left | M | 17 |
| NB3 | Non-tumorigenic Epileptic | Not determined | F | 27 |

Example 1

Assays Supporting the Oxidative Cellular Energy Production Process and Mitochondrial Activity of Cancer-Initiating FL1$^+$ Cell Population Anaerobic and aerobic pathways in cells is represented under FIG. 1. Glycolysis is a process which metabolizes glucose to pyruvate in the cytoplasm. Under hypoxic conditions, pyruvate in transformed in lactate by the LDH: 1 GLC→2 ATP Tricarboxilic Acid (TCA) combined to oxidative phosphorylation (OXPHOS) is a process which uses the pyruvate from the glycolysis, electron transfert via NADH and FADH2 to the respiratory chain complexes in mitochondria, and the proton gradient pump to generate ATP from ADP. Aerobic conditions: 1 GLC→36 ATP The metabolic pathway in cancer initiating cells was investigated by determining the following parameters:

Number of active mitochondria (such as M75-13): cells were harvested, dissociated, washed and incubated for 30 min at 37° C. with M75-13 diluted at 250 nM final in DMEM-F12-Glutamax 1/1000 penicillin/streptomycin. After staining, cells were washed twice with PBS1x and analysed on a FacsCan in the FL1 and FL3 channel. The percentage of Mito$^+$ cells (i.d. FL1$^+$ cells) was finally determined in the FL1 and FL1$^0$ cell populations.

Levels of NADH using the MTS oxido-reduction based reaction: Dissociated gliomaspheres were purified according to FL1$^+$ and FL1$^0$ cells as described in PCT/IB2008/054872. Levels of NADH were indirectly evaluated using AQ$_{ueous}$ One Solution Cell Proliferation Assay (Promega) according to manufacturer's instruction. Measures were performed on a 96-well plate reader (Biorad) at 490 nm.

Levels of lactate: CICs were sorted according to the protocol described in the PCT/IB2008/054872. 1.5 10$^5$ purified FL1$^+$ or/and FL1$^0$ cells were lysed in 100 μl sterile H$_2$O by repeating twice the following freezing-thawing cycle (5 min at −80° C., 2 min at 37° C.). Lysates were then centrifuged at 1,500 rpm for 5 min at 4° C., and supernatant were transferred in new 1.5 ml microtube. 3 μl were mixed with Lactate Oxidase (700 U/L), Peroxidase (508 U/L), DCBSA (2 mmol/L) and 4-aminoantipyrine (1.16 mmol/L) and analysed using the SYNCHRON system (Beckman Coulter) according to manufacturer's instruction.

Levels of glucose: CICs were sorted according to the protocol described in the PCT/IB2008/054872. 1.5 10$^5$ purified FL1$^+$ or/and FL1$^0$ cells were lysed in 100 μl sterile H$_2$O by repeating twice the following freezing-thawing cycle (5 min at −80° C., 2 min at 37° C.). Lysates were then centrifuged at 1,500 rpm for 5 min at 4° C., and supernatant were transferred in new 1.5 ml microtube. 10 μl were mixed with Glucose Oxidase (150 U/L), denatured Ethanol (5%), potassium iodide (0.04 mmol/L) and ammonium molybdate (0.036 mmol/L) and analysed using the SYNCHRON system (Beckman Coulter) according to manufacturer's instruction.

Levels of pyruvate: CICs were sorted according to the protocol described in the PCT/IB2008/054872. 1.5 10$^5$ purified FL1$^+$ or/and FL1$^0$ cells were lysed in 100 μl sterile H$_2$O by repeating twice the following freezing-thawing cycle (5 min at −80° C., 2 min at 37° C.). Lysates were then centrifuged at 1,500 rpm for 5 min at 4° C., and supernatant were transferred in new 1.5 ml microtube. Levels of lactate were determined by HPLC.

Levels of LD: CICs were sorted according to the protocol described in the PCT/IB2008/054872. 1.5 10$^5$ purified FL1$^+$ or/and FL1$^0$ cells were lysed in 100 μl sterile H$_2$O by repeating twice the following freezing-thawing cycle (5 min at −80° C., 2 min at 37° C.). Lysates were then centrifuged at 1,500 rpm for 5 min at 4° C., and supernatant were transferred in new 1.5 ml microtube. 13 μl were mixed with Lactate (50 mmol/L) and NAD (11 mmol/L) and analysed using the SYNCHRON system (Beckman Coulter) according to manufacturer's instruction.

Triplicate analyses of 3 independent set of sorted cells were done for each assays.

Figure 2:
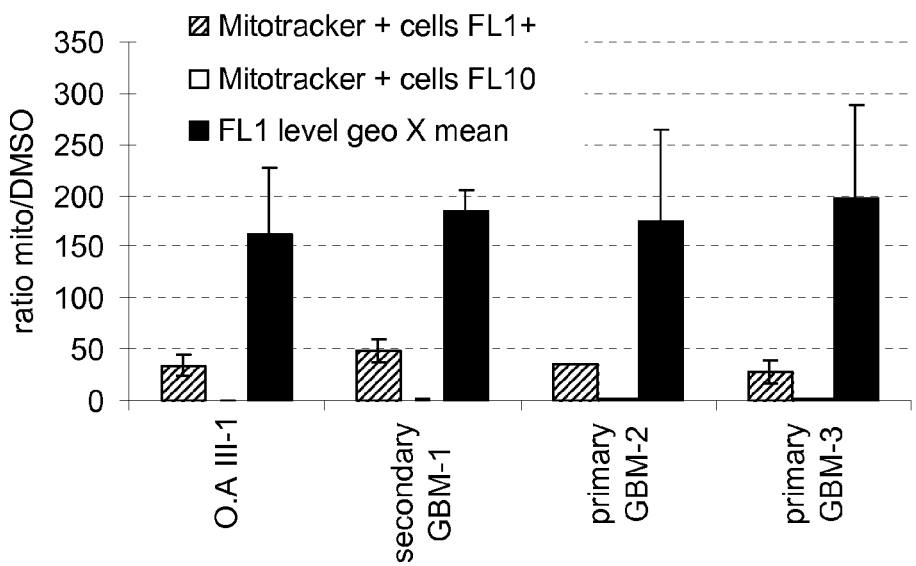
FIG. 2 represents parameters indicative of mitochondrial activity in cancer stem cells. A: percentage of $Mito^+$ cells (determined by quantifying the number of FL3 positive cells after incorporation of the M75-13 dye) in the $FL1^+$ (white background with black dashed lines) and $FL1^0$ cell populations (white) and level of FL1 autofluorescence in $FL1^+$ cells (black) measured by FACS in the FL1-H and FL3-H channel.
Figure 3:
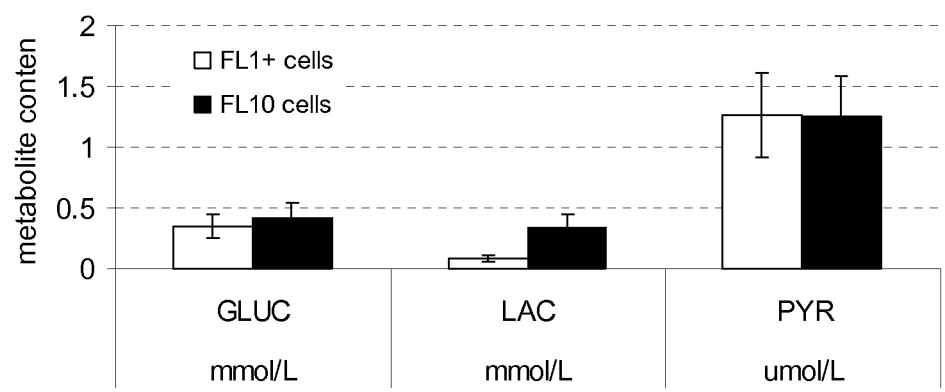
FIG. 3 shows the reduced glycolytic activity of $FL1^+$ cells as compared to $FL1^0$, primary glioma and normal brain cells. A: Levels of metabolite (LAC: lactate, PYR: pyruvate, GLUC: glucose) for $FL1^+$ and $FL1^0$ cells; B & C: Effect of lactate addition (LAC) on $FL1^+$ cell morphology by phase contrast imaging (B) and on the percentage of $FL1^0$ cells (C). Non treated (NT); Scale bar: 150 μM. D: Level of active Lactate Deshydrogenase (LD expressed in UI/L) in purified-$FL1^+$ and -$FL1^0$ cells.
Figure 3:
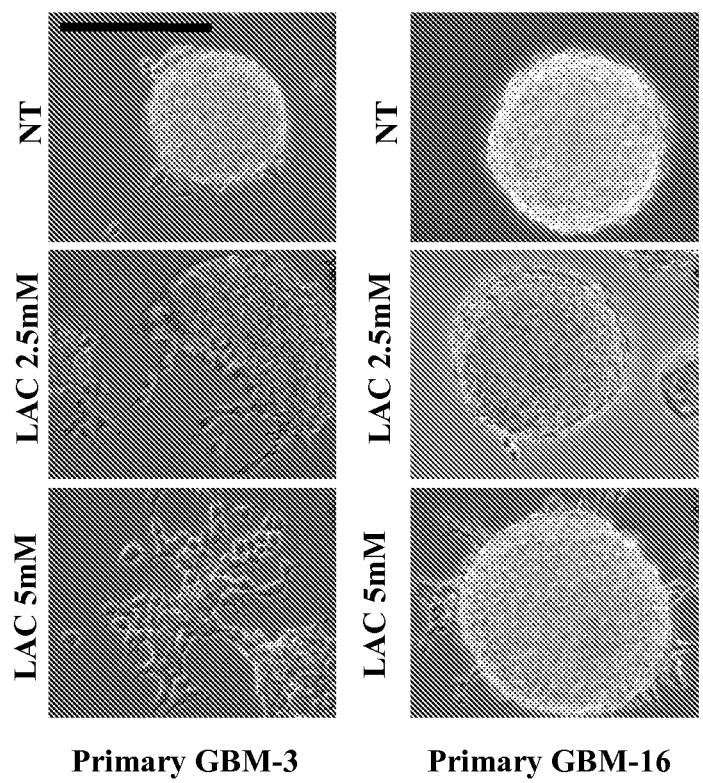

These experiments showed that FL1$^+$ cells are enriched for NADH levels, do contain a higher number of active mitochondria compared to FL1$^0$ cells and may therefore have a high metabolic activity (FIG. 2). Further, FL1$^+$ cells have low levels of lactate in vitro and in vivo compared to FL1$^0$ cells (FIG. 3A). The addition of exogeneous lactate along 10 days is sufficient to induce cell adhesion (FIG. 3B) and commits cells towards the FL1$^0$ phenotype (FIG. 3C). CICs have high levels of active LD compared to FL1$^0$ (FIG. 3D).

The effect of compounds known to activate the oxidative path ways in cells (DCA, which is known to activate the oxidative pathway and oxamate, known to inhibit cytosolic LDH3-5, see Michelakis et al., 2008, *Br J Cancer*, 99, 989-994 and Lemire et al., 2008, *PLoS ONE*, 3, e1550) were tested on CICs as follows:

For short term/dose response (48 hrs): Dissociated gliomasphere cells, adherent glioma and normal cells were plated at 10 cell/μl in DMEM-F12 Glutamax, BIT20% or B27 (1/50), Penicillin/streptomycin 1/1000, with reduced mitogens at 1 ng/ml or with reduced level of serum (2.5%).

For long term treatment/recovery assay (T10 and/or T20): Dissociated gliomasphere cells, adherent glioma and normal cells were plated at 2 cell/μl in DMEM-F12 Glutamax, Hepes 30 mM, BIT20% or B27 (1/50), Penicillin/streptomycin 1/1000, with reduced mitogens at 1 ng/ml or with reduced level of serum (2.5%).

For the recovery, cells were harvested, washed with PBS1x, and placed back into their standard media. (e.g. for gliomaspheres, in DMEM-F12 Glutamax, BIT20% or B27 (1/50), Hepes 30 mM, Penicillin/streptomycin 1% with mitogens at 10 ng/ml and for primary glioma cells and normal brain cells, DMEM-F12 Glutamax, 10% FBS, Penicillin/streptomycin 1%.

Figure 4:
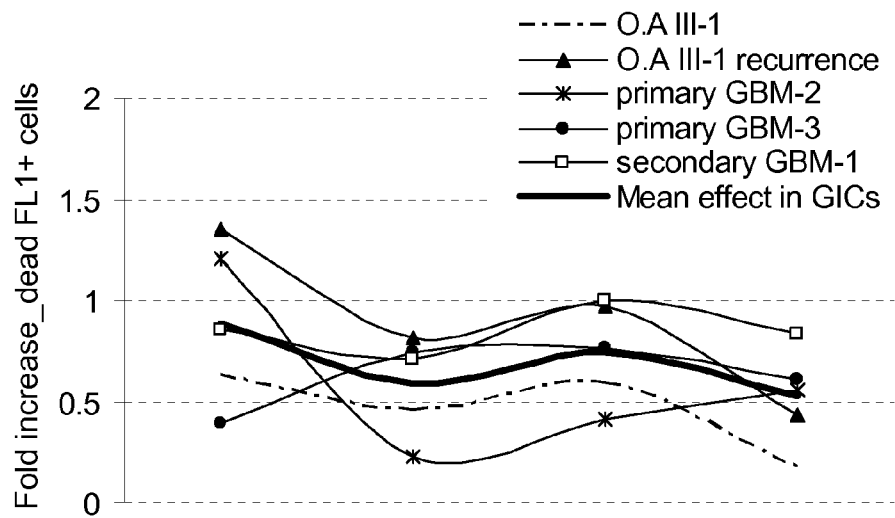
FIG. 4 shows the effect DCA or oxamate treatments on $FL1^+$ cells based on the ratio of percentage of dead $FL1^+$ cells in samples treated with the above agents as compared to a sample when treated the vehicle control. A: DCA treatment (activator of the oxidative pathway). B: oxamate treatment (inhibitor of cytosolic Lactate dehydrogenase 3-5 (LDH3-5).
Figure 4:
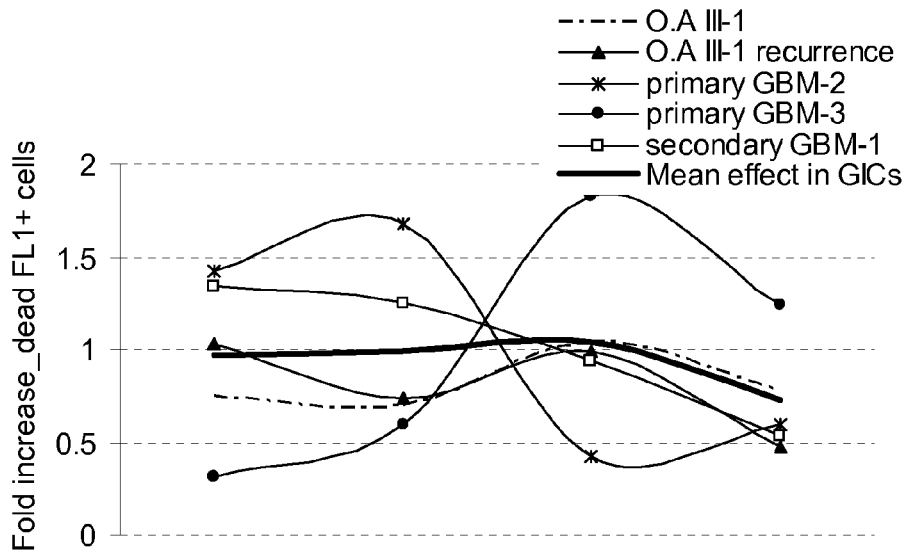

The results show that FL1$^+$ cells are not killed by agents pushing cells toward an active aerobic pathway or inhibiting the anaerobic pathway as shown by the ratio of FL1$^+$ cells which doesn't significant vary after exposure to increasing dose of DCA or oxamate, and even after 10 days (FIG. 4). As opposed, the FL1$^+$ cells display a tendency of being even healthier and less differentiating after such treatment. Therefore, it can be concluded that FL1$^+$ cells preferentially produce their energy using the aerobic pathway (TCA and oxidation phosphorylation-electron transport chain) in contrast to FL1$^0$ or FL1$^-$ cells, which are under an aerobic glycolysis system. Further, the metabolic switch from aerobic to aerobic glycolysis and commitment to differentiation are closely related and both are irreversible fate.

Example 2

Testing Potential Anti-Cancer Stem Cell Agents (Inhibitors)

Based on the results on the activity of the mitochondria, the contents of metabolite and the effect of inhibitors of the anaerobic energy production pathway (described in the Example 1), FL1+ cells are likely to preferentially produce their energy using the aerobic pathway in contrast to FL1° or FL1− cells, which are under an aerobic glycolysis system. Therefore, any agent harbouring an efficient capacity to inhibit the mitochondrial activity should impair the energy production within CICs, which in turn is likely to kill CICs. This was tested in an in vitro recurrence assay as represented under FIG. 5 and as follows:

For short term/dose response (48 hrs): Dissociated gliomasphere cells, adherent glioma and normal cells were plated at 10 cell/µl in DMEM-F12 Glutamax, BIT20% or B27 (1/50), Hepes 30 mM, Penicillin/streptomycin 1/1000, with reduced mitogens at 1 ng/ml or with reduced level of serum (2.5%).

For long term treatment/recovery assay (T10 and/or T20): Dissociated gliomasphere cells, adherent glioma and normal cells were plated at 2 cell/µl in DMEM-F12 Glutamax, Hepes 30 mM, BIT20% or B27 (1/50), Penicillin/streptomycin 1/1000, with reduced mitogens at 1 ng/ml or with reduced level of serum (2.5%).

For the recovery, cells were harvested, washed with PBS1x, and placed back into their standard media. (e.g. For gliomaspheres, in DMEM-F12 Glutamax, BIT20% or B27 (1/50), Penicillin/streptomycin 1/1000 with mitogens at 10 ng/ml and for primary glioma cells and normal brain cells, DMEM-F12 Glutamax, 10% FBS, Penicillin/streptomycin 1/1000.

The efficacy of a compound used to decrease and/or eradicate cancer stem cells (e.g. recurrence of the cancer stem cells) may be assayed by detecting the presence of stem cells in a cell sample after treatment with the agent or inhibitor according to the invention, for example by a method as described in PCT/IB2008/054872, i.e. comprising the following steps:

a) Providing a cancer stem cell sample which was treated by a compound or a method according to the invention;
b) Incubating the treated stem cell sample in a stem cell culture medium for an incubation period without treatment;
c) Selecting the viable cell population from the stem cell sample incubated under step (b);
d) Measuring the mean level of autofluorescence on the viable cell population isolated under step (c) by detecting, by fluorescence activated cell sorting, cells presenting autofluorescence emission in the FL1 channel upon laser beam excitation at a wavelength of or about 488 nm;
e) Isolating cells by fluorescence activated cell sorting cell which have a specific morphology (high FSC and low/middle SSC) and present autofluorescence emission in the FL1 channel upon laser beam excitation at a wavelength of or about 488 nm of the viable cell population isolated under step (c);
f) Isolating cells by fluorescence activated cell sorting which have a specific morphology (low/middle FSC and middle/high SSC), do not present autofluorescence emission in the FL1 channel under step (c) and present a slight positive shift in the cell fluorescence emission in the FL1 and/or FL4 channel upon laser beam excitation of the viable cell population isolated under step (c);
g) Calculating the percentage of autofluorescent viable cells by comparing the mean level of autofluorescence in the cancer stem cell sample provided under step (a) and the mean level of autofluorescence measured under step (d);
h) Calculating the percentage of the cell death by comparing the number of initial cells present in the cancer stem cell sample provided under step (a) and the resulting viable cell population isolated under step (c);
i) Calculating the percentage of viable FL1+ cells by comparing the number of initial FL1+ cells present in the cancer stem cell sample provided under step (a) and the resulting viable FL1+ cell population isolated under step (e);
j) Calculating the percentage of viable FL1° cells by comparing the number of initial FL1° cells present in the cancer stem cell sample provided under step (a) and the resulting viable FL1° cell population isolated under step (f);
k) Detecting spherogenicity of the cell populations detected under steps (e) and (f).
l) Determining the activity of the agent through its ability to inhibit cancer stem cells recurrence.

The compounds tested are summarized in Table 2 and 3.

The effect of γ-irradiation (FIG. 6 B1) and temozolomide (FIGS. 6 A1 & A2), the principal cytotoxic agent currently used for GBM were tested. In contrast to FBS-cultured glioma cells, ~40% of FL1+ cells resist to a Gy irradiation, survive and therefore recover within 30 days post-genotoxic stress, confirming that radiation mostly do not target the CICs sub-population but rather the rapidly dividing cells from the bulk. Prior temozolomide treatment, the methylation status of the MGMT promoter in gliomasphere cells was tested as described in Hegi et al., 2005, *N. Engl. J. Med.*, 352, 997-1003 predicting that gliomasphere cells should be sensitive to temozolomide. Nevertheless, even after 20 days treatment with temozolomide at 25 µM, more than 30% of FL1+ cells were still viable and therefore able to recover within 20 days (0.2<R<1).

Long term treatment with Erlotinib (inhibitor of the EGFR signalling pathway known for the treatment of non-small cell lung cancer, pancreatic cancer and several other types of cancer) at 5 µM is inducing cell death in more than 50% of FL1+ cells only in ⅔ GBM independently of the EGFR status, confirming that the amplification of the EGFR gene doesn't correlate with the responsiveness to EGFR kinase inhibitors such as Gefitinib or Erlotinib. Furthermore, all gliomasphere cultures were able to recover from the treatment within 10 days, suggesting that blocking the EGFR signaling pathway at the level of the receptor might be inefficient. Similar, but not identical, inhibition of mTOR using 1 µM temsirolimus or targeting developmental pathways like SHH-Gli or NOTCH (using 5 µM cyclopamine or 5 µM DAPT respectively) give rise to a decrease of the number of viable FL1+ cells. But again, those drugs were unable to eradicate the whole FL1+ cell population, so that they recover easily within 10 days even after 20 days treatment.

Inhibition of either complex I (Rotenone), III (Antimycin A), or IV (oligomycin A/B) of the mitochondria kills the FL1+ cell population (FIG. A to C). Blocking the complex IV using oligomycin A/B eradicate any kind of brain cells including normal and glioma ones (FIG. 6 C1 & C2) unlike blocking the complex I (FIG. 6 A1 &A2) and III (FIG. 6 B1 & B2). More specifically, the inhibition of the complex III (using for example Antimycin A) might be more appropriate for CICs as it does not really affect the viability of normal brain cells.

As the metabolism of CICs differs from the tumour bulk cells and from normal brain cells, the combination of specific agent for debulking (eradicating FL1° and FL1− cells) and specific for CICs (eradicating FL1+ cells) would be an advantageous strategy to eradicate growth and recurrence of human glioma.

Condition media for the treatment and the recovery periods, and criteria required for evaluating the efficiency of an agent to kill the CICs (please refer to the FIG. 5A).

The invention claimed is:
1. A method of treating tumours presenting glioma initiating cells in a subject who has undergone a prior removal of a tumour glioma bulk, wherein preferably said removal of a tumour glioma bulk is segmental resection of a tumour glioma bulk, said method comprises the administration of a therapeutically effective amount of an inhibitor of the activity of Complex (I) mitochondrial electron transport chain selected from the group consisting of Rotenone, Myxothiazole, Stigmatellin, Piericidin and combinations thereof, derivatives thereof, and pharmaceutically acceptable salts thereof.

2. The method of treating tumours presenting glioma initiating cells in a subject who has undergone a prior removal of a tumour glioma bulk of claim 1, wherein said therapeutically effective amount is up to 10 times $IC_2$ dose, said $IC_2$ dose being a range of 0.157 to 0.315 mg/kg.

3. The method of treating tumours presenting glioma initiating cells in a subject who has undergone a prior removal of a tumour glioma bulk of claim 1, wherein said method further comprises the step of treatment by standard radiotherapy and/or chemotherapy before or after the administration of a therapeutically effective amount of said inhibitor of the activity of Complex (I) of the mitochondrial electron transport chain selected from the group consisting of Rotenone, Myxothiazole, Stigmatellin, Piericidin and combinations thereof, derivatives thereof, and pharmaceutically acceptable salts thereof.

* * * * *